United States Patent
Mishra et al.

(10) Patent No.: US 11,123,011 B1
(45) Date of Patent: Sep. 21, 2021

(54) WEARABLE SYSTEMS, DEVICES, AND METHODS FOR MEASUREMENT AND ANALYSIS OF BODY FLUIDS

(71) Applicant: Nix, Inc., Boston, MA (US)

(72) Inventors: Shawn Mishra, Lawrence, MA (US); Kenneth Ritsher, Lowell, MA (US); Meridith Unger Cass, Medford, MA (US)

(73) Assignee: Nix, Inc., Medford, MA (US)

( * ) Notice: Subject to any disclaimer, the term of this patent is extended or adjusted under 35 U.S.C. 154(b) by 0 days.

(21) Appl. No.: 16/827,349

(22) Filed: Mar. 23, 2020

(51) Int. Cl.
| | |
|---|---|
| *A61F 9/008* | (2006.01) |
| *A61B 5/00* | (2006.01) |
| *A61B 5/1477* | (2006.01) |
| *A61B 5/0537* | (2021.01) |
| *A61B 5/01* | (2006.01) |

(52) U.S. Cl.
CPC .............. *A61B 5/4875* (2013.01); *A61B 5/01* (2013.01); *A61B 5/0537* (2013.01); *A61B 5/1477* (2013.01); *A61B 5/4266* (2013.01); *A61B 5/6833* (2013.01); *A61B 2562/0215* (2017.08)

(58) Field of Classification Search
CPC ....... A61B 5/4875; A61B 5/01; A61B 5/0537; A61B 5/1477; A61B 5/4266; A61B 5/6833; A61B 2562/0215
See application file for complete search history.

(56) References Cited

U.S. PATENT DOCUMENTS

| | | |
|---|---|---|
| 3,139,085 A | 6/1964 | Custance et al. |
| 4,190,056 A | 2/1980 | Tapper et al. |
| 4,190,060 A | 2/1980 | Greenleaf et al. |
| 4,195,641 A | 4/1980 | Joines et al. |
| 4,203,450 A | 5/1980 | Kegel |
| 4,266,556 A | 5/1981 | Barlow et al. |

(Continued)

FOREIGN PATENT DOCUMENTS

| | | |
|---|---|---|
| CA | 2780747 A1 | 5/2010 |
| CA | 2910385 A1 | 11/2014 |

(Continued)

OTHER PUBLICATIONS

Liu et al., A wearable conductivity sensor for wireless real-time sweat monitoring, 2016, Sensors and Actuators B: Chemical, 227, 35-42 (Year: 2016).*

(Continued)

*Primary Examiner* — Michael W Kahelin
*Assistant Examiner* — George E Banis
(74) *Attorney, Agent, or Firm* — Cooley LLP

(57) ABSTRACT

Methods, systems, and devices are described herein for various embodiments of using a sample analysis system to analyze a sample of bodily fluid from a user to determine parameters associated with the user including states of hydration, dehydration, rehydration, electrolyte loss, wellness, recovery, and the like. In some embodiments, the methods disclosed can be implemented using a device worn by a user, and operatively coupled to a sample analysis system configured to collect a sample of bodily fluid, and measure and analyze the bodily fluid to determine a property of the bodily fluid and/or a physiological/wellness parameter (e.g., degree of hydration, electrolyte losses, perspiration rate, etc.) of the user.

20 Claims, 23 Drawing Sheets

(56) References Cited

U.S. PATENT DOCUMENTS

| | | |
|---|---|---|
| 4,542,751 A | 9/1985 | Webster et al. |
| 4,638,512 A | 1/1987 | Frankel |
| 4,756,314 A | 7/1988 | Eckenhoff et al. |
| 5,131,390 A | 7/1992 | Sakaguchi et al. |
| 5,174,656 A | 12/1992 | Dotan |
| 5,757,278 A | 5/1998 | Itsumi |
| 5,976,499 A | 11/1999 | Rubenstein et al. |
| 6,132,975 A | 10/2000 | Kanan et al. |
| 6,198,953 B1 | 3/2001 | Webster et al. |
| 6,269,265 B1 | 7/2001 | Anderson |
| 6,276,155 B2 | 8/2001 | Siman-Tov et al. |
| 6,309,535 B1 | 10/2001 | Williams et al. |
| 6,332,225 B1 | 12/2001 | Casey |
| D453,985 S | 3/2002 | Casey |
| 6,443,892 B1 | 9/2002 | Kidwell |
| 6,517,497 B2 | 2/2003 | Rymut et al. |
| 6,585,986 B2 | 7/2003 | Matsuzaki et al. |
| 6,780,307 B2 | 8/2004 | Kidwell |
| 6,943,662 B2 | 9/2005 | Tanimura |
| 7,964,409 B1 | 6/2011 | Kennedy |
| 8,215,192 B2 | 7/2012 | Erez et al. |
| 8,273,021 B2 | 9/2012 | Jang et al. |
| 8,372,726 B2 | 2/2013 | de Graff et al. |
| 8,551,608 B2 | 10/2013 | Kawakami et al. |
| 8,934,954 B2 | 1/2015 | Brunswick et al. |
| 9,113,559 B2 | 8/2015 | Heikenfeld et al. |
| 9,200,165 B2 | 12/2015 | Imokawa et al. |
| 9,226,730 B2 | 1/2016 | Briscoe et al. |
| 9,339,225 B2 | 5/2016 | Kennedy |
| 9,456,650 B1 | 10/2016 | Boyce |
| D781,270 S | 3/2017 | Li et al. |
| 9,603,560 B2 | 3/2017 | Monty et al. |
| 9,625,705 B2 | 4/2017 | Dean et al. |
| 9,662,069 B2 | 5/2017 | De Graff et al. |
| 9,677,919 B2 | 6/2017 | Kielb et al. |
| 9,704,908 B2 | 7/2017 | Graff et al. |
| 9,723,122 B2 | 8/2017 | Ghaffari et al. |
| D797,379 S | 9/2017 | Patel et al. |
| 9,757,050 B2 | 9/2017 | Ghaffari et al. |
| 9,801,557 B2 | 10/2017 | Ghaffari et al. |
| 2003/0127706 A1 | 7/2003 | Tanimura |
| 2003/0199743 A1 | 10/2003 | Berlin |
| 2005/0101252 A1 | 5/2005 | Carvalho et al. |
| 2006/0249389 A1 | 11/2006 | Fenn et al. |
| 2006/0253011 A1 | 11/2006 | Edmonson et al. |
| 2007/0056101 A1 | 3/2007 | Mahajan et al. |
| 2008/0166029 A1 | 7/2008 | Presura |
| 2008/0275310 A1 | 11/2008 | Kim |
| 2009/0269003 A1 | 10/2009 | Scully et al. |
| 2010/0063372 A1 | 3/2010 | Potts et al. |
| 2010/0130843 A1 | 5/2010 | Caceres Galvez et al. |
| 2010/0179403 A1 | 7/2010 | Martinsen et al. |
| 2010/0302004 A1 | 12/2010 | Winstead et al. |
| 2011/0152718 A1 | 6/2011 | Revol-Cavalier |
| 2011/0215931 A1 | 9/2011 | Callsen et al. |
| 2012/0042666 A1 | 2/2012 | Besore |
| 2012/0065937 A1 | 3/2012 | de Graff et al. |
| 2012/0252046 A1* | 10/2012 | Fei .................. A61B 5/14532 435/14 |
| 2013/0033476 A1 | 2/2013 | Dean et al. |
| 2013/0092543 A1 | 4/2013 | Heikenfeld |
| 2013/0125643 A1 | 5/2013 | Batty et al. |
| 2013/0144136 A1 | 6/2013 | Rymut |
| 2013/0192356 A1 | 8/2013 | de Graff et al. |
| 2013/0248380 A1 | 9/2013 | Cui |
| 2013/0332114 A1 | 12/2013 | Dasu et al. |
| 2014/0001058 A1 | 1/2014 | Ghaffari et al. |
| 2014/0022746 A1 | 1/2014 | Hsu |
| 2014/0221792 A1 | 8/2014 | Miller et al. |
| 2014/0257064 A1 | 9/2014 | Einck et al. |
| 2015/0057515 A1 | 2/2015 | Hagen et al. |
| 2015/0067066 A1 | 3/2015 | Radhakrislman |
| 2015/0108341 A1 | 4/2015 | Shishika et al. |
| 2015/0112164 A1 | 4/2015 | Heikenfeld et al. |
| 2015/0112165 A1 | 4/2015 | Heikenfeld |
| 2015/0141775 A1 | 5/2015 | Macaluso et al. |
| 2015/0165206 A1* | 6/2015 | Venkatesan .......... A61N 1/0531 607/62 |
| 2015/0289775 A1 | 10/2015 | Chon et al. |
| 2015/0289820 A1 | 10/2015 | Miller et al. |
| 2015/0305675 A1 | 10/2015 | Miller et al. |
| 2015/0335254 A1 | 11/2015 | Fastert et al. |
| 2015/0359469 A1 | 12/2015 | Jacobs et al. |
| 2016/0051191 A1 | 2/2016 | Miller et al. |
| 2016/0132732 A1 | 5/2016 | Gunther et al. |
| 2016/0213424 A1 | 7/2016 | Ghaffari et al. |
| 2016/0228640 A1 | 8/2016 | Pindado et al. |
| 2016/0232807 A1 | 8/2016 | Ghaffari et al. |
| 2016/0235374 A1 | 8/2016 | Miller et al. |
| 2016/0240061 A1 | 8/2016 | Li et al. |
| 2016/0249847 A1 | 9/2016 | Kennedy |
| 2016/0287148 A1 | 10/2016 | Pizer et al. |
| 2016/0294789 A1 | 10/2016 | Houghton et al. |
| 2016/0309594 A1 | 10/2016 | Hsu |
| 2016/0371957 A1 | 12/2016 | Ghaffari et al. |
| 2016/0374598 A1 | 12/2016 | Heikenfeld et al. |
| 2017/0014043 A1 | 1/2017 | McDonnell |
| 2017/0014067 A1 | 1/2017 | Peppou et al. |
| 2017/0048975 A1 | 2/2017 | Johnson et al. |
| 2017/0049397 A1 | 2/2017 | Sun et al. |
| 2017/0071518 A1 | 3/2017 | Xavier Da Silveira et al. |
| 2017/0079589 A1 | 3/2017 | Ghaffari et al. |
| 2017/0083312 A1 | 3/2017 | Pindado et al. |
| 2017/0086715 A1 | 3/2017 | Iuele et al. |
| 2017/0086749 A1 | 3/2017 | Ghaffari et al. |
| 2017/0095183 A1 | 4/2017 | Heikenfeld |
| 2017/0095184 A1 | 4/2017 | Heikenfeld |
| 2017/0095732 A1 | 4/2017 | Ghaffari et al. |
| 2017/0100102 A1 | 4/2017 | Heikenfeld |
| 2017/0105795 A1 | 4/2017 | Lee et al. |
| 2017/0110417 A1 | 4/2017 | Arora et al. |
| 2017/0143232 A1 | 5/2017 | Yamaji |
| 2017/0156641 A1 | 6/2017 | Nyberg et al. |
| 2017/0172470 A1 | 6/2017 | Begtrup et al. |
| 2017/0172484 A1 | 6/2017 | Sonner et al. |
| 2017/0173262 A1* | 6/2017 | Veltz .................. A61B 5/0022 |
| 2017/0181659 A1 | 6/2017 | Rafferty et al. |
| 2017/0186727 A1 | 6/2017 | Dalal et al. |
| 2017/0188942 A1 | 7/2017 | Ghaffari et al. |
| 2017/0191521 A1 | 7/2017 | Hopkins |
| 2017/0200670 A1 | 7/2017 | Rafferty et al. |
| 2017/0215773 A1 | 8/2017 | Heikenfeld et al. |
| 2017/0220772 A1* | 8/2017 | Vleugels ............... A61B 5/4866 |
| 2017/0223844 A1 | 8/2017 | Pizer et al. |
| 2017/0238854 A1 | 8/2017 | Henshaw |
| 2017/0243464 A1 | 8/2017 | Diaz |
| 2017/0244285 A1 | 8/2017 | Raj et al. |
| 2017/0245788 A1 | 8/2017 | Heikenfeld |
| 2017/0296114 A1* | 10/2017 | Ghaffari ............. A61B 5/14517 |
| 2017/0303788 A1 | 10/2017 | Xavier Da Silveira et al. |
| 2018/0064377 A1* | 3/2018 | Rogers .................. G01N 33/50 |
| 2019/0117170 A1* | 4/2019 | Begtrup ............... A61B 5/4875 |
| 2019/0231236 A1* | 8/2019 | Heikenfeld ........ A61B 5/14532 |

FOREIGN PATENT DOCUMENTS

| | | |
|---|---|---|
| CA | 2913483 A1 | 12/2014 |
| CA | 2927213 A1 | 4/2015 |
| CA | 2959699 A1 | 4/2016 |
| CA | 2965658 A1 | 5/2016 |
| CN | 105997071 A | 10/2016 |
| EP | 1700147 B1 | 10/2009 |
| EP | 2587240 A2 | 5/2013 |
| EP | 2902294 A2 | 8/2015 |
| EP | 2938982 B1 | 11/2018 |
| EP | 2834007 B1 | 6/2019 |
| EP | 3148415 B1 | 10/2019 |
| JP | 2014-138645 A | 7/2014 |
| JP | 2015-154928 A | 8/2015 |
| JP | 2015-200671 A | 11/2015 |
| JP | 2016-006880 A | 1/2016 |
| JP | 2016-154017 A | 8/2016 |
| JP | 2016-213515 A | 12/2016 |
| JP | 2017-035505 A | 2/2017 |

(56) References Cited

FOREIGN PATENT DOCUMENTS

| | | |
|---|---|---|
| JP | 2017-108160 A | 6/2017 |
| WO | WO-2002073708 A2 | 9/2002 |
| WO | WO-2005002006 A2 | 1/2005 |
| WO | WO-2005114740 A1 | 12/2005 |
| WO | WO-2006017129 A2 | 2/2006 |
| WO | WO-2006121597 A2 | 11/2006 |
| WO | WO-2008039832 A2 | 4/2008 |
| WO | WO-2010042957 A2 | 4/2010 |
| WO | WO-2010102310 A2 | 9/2010 |
| WO | WO-2010104606 A1 | 9/2010 |
| WO | WO-2011127331 A2 | 10/2011 |
| WO | WO-2012091776 A2 | 7/2012 |
| WO | WO-2013010171 A1 | 1/2013 |
| WO | WO-2013049716 A1 | 4/2013 |
| WO | WO-2014039794 A2 | 3/2014 |
| WO | WO-2014197443 A1 | 12/2014 |
| WO | WO-2015020367 A1 | 2/2015 |
| WO | WO-2015054312 A1 | 4/2015 |
| WO | WO-2015054506 A2 | 4/2015 |
| WO | WO-2015058055 A1 | 4/2015 |
| WO | WO-2015077559 A1 | 5/2015 |
| WO | WO-2015080991 A1 | 6/2015 |
| WO | WO-2015102951 A2 | 7/2015 |
| WO | WO-2015103483 A1 | 7/2015 |
| WO | WO-2015103580 A2 | 7/2015 |
| WO | WO-2015138712 A2 | 7/2015 |
| WO | WO-2015127458 A1 | 8/2015 |
| WO | WO-2015134588 A1 | 9/2015 |
| WO | WO-2015184072 A1 | 12/2015 |
| WO | WO-2015184084 A2 | 12/2015 |
| WO | WO-2015184097 A2 | 12/2015 |
| WO | WO-2016003482 A1 | 1/2016 |
| WO | WO-2016007944 A2 | 1/2016 |
| WO | WO-2016030869 A1 | 3/2016 |
| WO | WO-2016048888 A1 | 3/2016 |
| WO | WO-2016089957 A1 | 6/2016 |
| WO | WO-2016130905 A1 | 8/2016 |
| WO | WO-2016134235 A1 | 8/2016 |
| WO | WO-2016134306 A1 | 8/2016 |
| WO | WO-2016138087 A1 | 9/2016 |
| WO | WO-2016140961 A1 | 9/2016 |
| WO | WO-2016142359 A1 | 9/2016 |
| WO | WO-2016144529 A1 | 9/2016 |
| WO | WO-2016187536 A1 | 11/2016 |
| WO | WO-2016191594 A1 | 12/2016 |
| WO | WO-2016197085 A1 | 12/2016 |
| WO | WO-2016197116 A1 | 12/2016 |
| WO | WO-2016205385 A1 | 12/2016 |
| WO | WO-2017015000 A1 | 1/2017 |
| WO | WO-2017019573 A1 | 2/2017 |
| WO | WO-2017019602 A1 | 2/2017 |
| WO | WO-2017031393 A1 | 2/2017 |
| WO | WO-2017044617 A1 | 3/2017 |
| WO | WO-2017044731 A1 | 3/2017 |
| WO | WO-2017053919 A1 | 3/2017 |
| WO | WO-2017062508 A1 | 4/2017 |
| WO | WO-2017070640 A1 | 4/2017 |
| WO | WO-2017070641 A1 | 4/2017 |
| WO | WO-2017075402 A1 | 5/2017 |
| WO | WO-2017095861 A1 | 6/2017 |
| WO | WO-2017112023 A2 | 6/2017 |
| WO | WO-2017123954 A1 | 7/2017 |
| WO | WO-2017189612 A1 | 11/2017 |
| WO | WO-2020/102439 A1 | 5/2020 |

OTHER PUBLICATIONS

Baker, L.B. et al. (2019) "Exercise intensity effects on total sweat electrolyte losses and regional vs. whole-body sweat [Na+], [Cl−], and [K+]" Eur J Appl Physiol, 119:361-375.

Del Coso, J. et al. (2013) "Influence of body mass loss and myoglobinuria on the development of muscle fatigue after a marathon in a warm environment" Appl Physiol Nutr Metab, 38:286-291.

Gopinathan, P.M. et al. "Role of Dehydration in Heat Stress-Induced Variations in Mental Performance" Archives of Environmental Health, 43(1):15-17.

Holmes, N. et al. (2016) "The Effect of Exercise Intensity on Sweat Rate and Sweat Sodium and Potassium Losses in Trained Endurance Athletes" Ann Sports Med Res, 3(2):1063, 4 pages.

International Search Report and Written Opinion, dated Feb. 5, 2020, in International Patent Application No. PCT/US2019/061301, filed Nov. 13, 2019 by Nix, Inc.; 17 pages.

Judelson, D.A. et al. (2007) "Hydration and Muscular Performance Does Fluid Balance Affect Strength, Power and High-Intensity Endurance?" Sports Med, 37(10):907-921.

Liu, G. et al (Dec. 15, 2015) "A wearable conductivity sensor for wireless real-time sweat monitoring" Sensors and Actuators B: Chemical, 227:35-42.

Martín, A. et al. (Dec. 22, 2017) "Epidermal Microfluidic Electrochemical Detection System: Enhanced Sweat Sampling and Metabolite Detection" ACS Sensors, 2(12):1860-1868.

Maughan, R.J. (2003) "Impact of mild dehydration on wellness and on exercise performance" Eur J Clin Nutr, 57(Suppl 2): S19-S23.

Niedermann, R. et al. (2014) "Prediction of human core body temperature using non-invasive measurement methods" Int J Biometerol, 58:7-15.

Nyein, H.Y.Y. et al. (May 9, 2018) "A Wearable Microfluidic Sensing Patch for Dynamic Sweat Secretion Analysis" ACS Sensors, 3(5):944-952.

Summers, R.L. et al. (2010) "Ultrasound measurements of lower extremity soft tissue and interstitial fluid thickness may be used as an early indicator of dehydration" Crit Ultrasound, 2:43-45.

* cited by examiner

| | Sweat [Na+] | | | Sweat [Cl] | | | Sweating Rate | | |
|---|---|---|---|---|---|---|---|---|---|
| | Significant increase in absolute values from LOW to MOD? (ES) | Significant change in REG-WB Ratio from LOW to MOD? (ES) | Significant effect of intensity on regression model? | Significant increase in absolute values from LOW to MOD? (ES) | Significant change in REG-WB Ratio from LOW to MOD? (ES) | Significant effect of intensity on regression model? | Significant increase in absolute values from LOW to MOD? (ES) | Significant change in REG-WB Ratio from LOW to MOD? (ES) | Significant effect of intensity on regression model? |
| Whole Body | Yes (1.15) | --- | --- | Yes (1.23) | --- | --- | Yes (1.50) | --- | --- |
| Dorsal Wrist | Yes (1.20) | No (0.23) | No | Yes (1.32) | No (0.65) | No | No (0.85) | No (0.14) | No |
| Ventral Wrist | Yes (1.12) | No (0.07) | Yes | Yes (1.27) | No (0.37) | Yes | No (1.30) | No (0.42) | Yes |
| Dorsal Forearm | Yes (1.09) | No (0.03) | No | Yes (1.18) | No (0.35) | No | No (1.21) | No (0.37) | No |
| Ventral Forearm | Yes (0.93) | No (0.05) | Yes | Yes (1.06) | No (0.37) | No | No (1.30) | No (0.25) | No |
| Triceps | Yes (1.00) | No (0.48) | Yes | Yes (1.15) | No (0.25) | No | No (0.83) | No (0.01) | Yes |
| Chest | Yes (1.21) | No (0.15) | Yes | Yes (1.34) | No (0.46) | No | No (1.08) | No (0.37) | Yes |
| Scapula | Yes (1.17) | No (0.34) | No | Yes (1.25) | No (0.09) | No | No (1.10) | No (0.04) | Yes |
| Lower Back | Yes (0.84) | No (0.86) | Yes | Yes (1.02) | No (0.13) | Yes | No (0.63) | No (0.40) | Yes |
| Ventral Thigh | Yes (0.65) | No (0.96) | Yes | Yes (0.79) | No (0.39) | Yes | No (0.73) | No (0.72) | Yes |
| Calf | Yes (0.58) | No (0.81) | Yes | No (0.74) | No (0.17) | Yes | No (0.78) | No (0.22) | Yes |
| Forehead | Yes (1.24) | No (0.21) | No | Yes (1.31) | No (0.31) | No | Yes (0.92) | No (0.47) | Yes |
| 11-Site | Yes (1.06) | No (0.33) | No | Yes (1.16) | No (0.18) | No | No (1.20) | No (0.17) | No |

FIG. 22

WEARABLE SYSTEMS, DEVICES, AND METHODS FOR MEASUREMENT AND ANALYSIS OF BODY FLUIDS

BACKGROUND

Embodiments described herein relate to systems, devices, and methods for use in the near instantaneous and cumulative measurement and analysis of body fluids and potential analytes contained therein. Embodiments described herein also relate to the implementation of a real-time hydration detection system and hydration strategizing system for use during activity.

SUMMARY

Systems, devices and methods are described herein for various embodiments of a sample analysis system that is worn by a user, the sample analysis system configured to collect a sample of bodily fluid, and measure and analyze the bodily fluid to determine a property of the bodily fluid and/or a physiological/wellness parameter (e.g., degree of hydration, electrolyte losses, perspiration rate, etc.) of the user.

BRIEF DESCRIPTION OF THE FIGURES

FIG. 22 is an example table showing changes in ion concentration in sweat samples obtained from multiple locations of the body of users performing low and moderate levels of activity.

DETAILED DESCRIPTION

Figure 1:
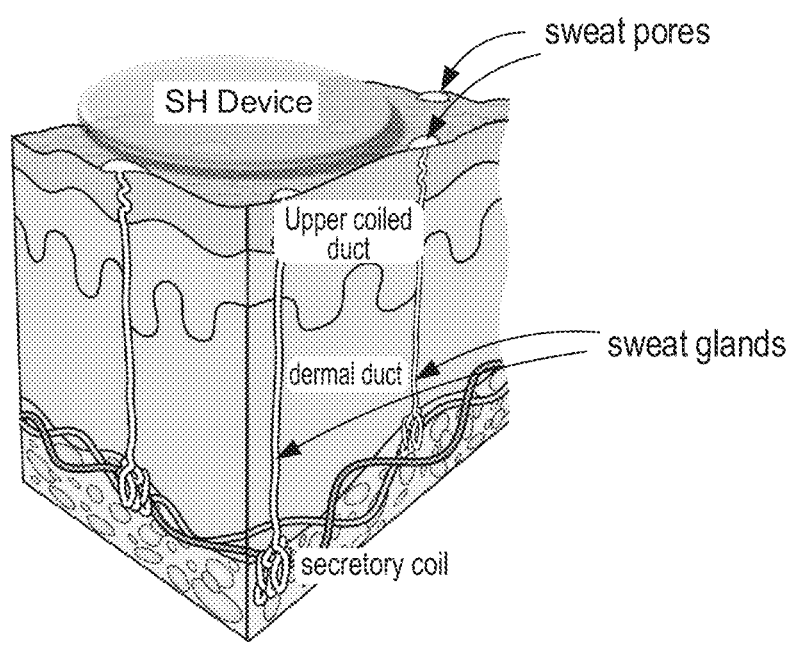
FIG. 1 is a schematic illustration of an example use of a sample handling device on a skin surface of a user, according to an embodiment.

Embodiments disclosed include a method comprising collecting a sample of bodily fluid in a sample collection region of a device and directing a portion of the sample of bodily fluid from the sample collection region to a first electrochemical interface, the first electrochemical interface including an excitation electrode and a sensing electrode. The method includes applying an excitation signal through the excitation electrode to the portion of the sample of bodily fluid at the first electrochemical interface and sensing a response signal in response to the applying the excitation signal. The method further includes measuring data associated with an instance of an electrochemical property related to the portion of the sample of bodily fluid based on the response signal.

Embodiments disclosed include a system comprising a memory storing a set of instructions, and a processor coupled to the memory and configured to execute the instructions stored in the memory. The processor is configured to receive, at a first time point, a first response signal obtained from a first portion of a sample bodily fluid collected from a user, and in contact with a first electrochemical interface of a device associated with the system. The processor is configured to receive, at a second time point, a second response signal obtained from a second portion of the sample bodily fluid, and in contact with a second electrochemical interface of the device associated with the system. The processor is further configured to receive information related to a distance between the first electrochemical interface and the second electrochemical interface and the distance being traversed by a flow of the sample bodily fluid. The processor is further configured to calculate, based on the first response signal, the second response signal and the distance, a flow rate of the sample bodily fluid through a flow channel included in the device.

Embodiments disclosed include an apparatus comprising a sample collection region having an inlet, an access port in fluidic communication with the sample collection region, and a flow channel, in fluid communication with the access port. The sample collection region is configured to receive an initial volume of bodily fluid via the inlet. The flow channel is configured to direct a portion of the initial volume of bodily fluid towards a set of electrodes. The set of electrodes includes an excitation electrode and a sensing electrode. The excitation electrode is configured to apply an excitation signal to the portion of the initial volume of bodily fluid, and the sensing electrode is configured to receive a response signal from the portion of the initial volume of bodily fluid in response to the excitation signal. The sensing electrode is further configured to transmit the response signal to a processor to calculate an impedance associated with the portion of the initial volume of bodily fluid.

Embodiments described herein relate to systems, devices, and methods for use in the measurement and analysis of bodily fluids using wearable system of measurement and analysis. A sample analysis system can be configured to collect a sample of bodily fluid, and measure and analyze the bodily fluid to determine a property (e.g., impedance, osmolality) of the bodily fluid and/or a physiological/wellness parameter (e.g., degree of hydration, electrolyte losses, perspiration rate, etc.) of the user. For example, systems and devices as described herein can collect a sample of bodily fluid (e.g., sweat) and measure the impedance of the bodily fluid. The impedance measurement can then be used to determine and/or predict a property (e.g., osmolality) of the sweat. In some instances, the sample of bodily fluid can be collected as a continuous or semi-continuous flow, i.e. as produced by the body.

In some instances, the collected bodily fluid can be directed to flow along a controlled flow path and the measurement of impedance of the bodily fluid can be made in two or more test regions or locations associated with the controlled flow path. The measurements of impedance and the known features of the controlled flow path (e.g., volume, length, distance between test regions, etc.,) can be used to determine a linear and/or a volumetric flow rate associated with the bodily fluid. The volumetric flow rate can be a regional or localized flow rate that is related to the portion of the user's body where the device to collect the bodily fluid is worn. In some implementations, methods described herein can be used to extrapolate from the localized flow rate of a region of a user's body to a whole-body flow rate, and/or a whole-body rate of perspiration.

Without wishing to be bound by any particular theory, it is believed that the electrolyte content of the sweat is a primary contributor to the osmolality of the sweat; therefore, the determined osmolality can be used to estimate the electrolyte content of the sweat. The sweat data can then be used to determine or predict a physiological parameter (e.g., degree of hydration, electrolyte losses, perspiration rate, etc.) of the user.

Although the system is described above as being used to determine the electrolyte content of sweat based on an impedance measurement, the system can also be used to determine the osmolality of other bodily fluids and/or secretions including, for example, saliva, tears, urine, breast milk, etc., which can provide insights about hydration or other physiological parameters of the users. In addition, without wishing to be bound by any particular theory, some scientific evidence suggests that the osmolality of breast milk can be used to determine the nutritional content of the breast milk. Thus, similar to the analysis described above, the system can be used to measure the impedance of breast milk, which can be correlated to the osmolality of breast milk to provide insights about its nutritional content.

As described herein, individuals such as athletes, military service members, laborers, children, the elderly, patients under critical care, and the general population can immensely benefit from timely monitoring of their physiological state and well-being, using suitable indicators of a state of wellness, and timely intervention or correction based on the monitoring. Some example secondary indicators of physiological state and well-being include a degree of hydration, body water losses, and indications of electrolyte losses, which can affect physical and cognitive performance.

Studies show that up to 87% of endurance athletes are physically impaired during their workouts and competitions due to dehydration, despite ample access to fluids. Dehydration can cause decreased blood pressure, increase heart rate, increased respiratory rate, and decreased blood flow to extremities. These physiological changes can lead to cardiorespiratory stress, impaired thermoregulation, and fatigue—all of which have a significant impact on patient wellness and/or athletic performance. Because the symptoms of mild dehydration are subtle—often imperceptible—individuals suffer the consequences without always knowing it.

For example, under some circumstances bodily fluids when lost and not adequately replaced can lead to dehydration which may decrease blood pressure and impair circulation of blood and components carried by blood (e.g., oxygen, nutrients, etc.). In some instances, the body undergoing dehydration might compensate by initiating one or more physiological responses that might result in undesired effects. For example, to compensate for reduced circulation the body might respond with increased heart rate leading to cardiac stress and fatigue; or increased respiratory rate resulting in respiratory stress and fatigue. In some instances, the body might respond by decreasing blood flow to extremities (e.g., skin, appendages, muscles) to conserve blood flow for the vital organs. This might cause impaired thermoregulation and increased risk of heat illness, and/or cause muscle cramping and fatigue. In some circumstances, the body might respond to dehydration by constricting capillaries or otherwise redirecting circulation to decrease blood flow to the gastrointestinal tract to conserve blood flow to the vital organs. This may result in impaired fluid absorption, gastrointestinal distress (vomiting). In circumstances where dehydration continues to worsen, the body may further deteriorate with rise in core body temperature resulting in heat injury, and blood flow to vital organs may be further restricted resulting in multi-system organ failure and death.

Dehydration causes physical performance to deteriorate after just 1% of body weight loss and worsens exponentially with each percent lost. Dehydration corresponding to 2% of body weight is widely recognized as the threshold at which statistically significant performance impairment is observed (approximately 29% impairment). Performance is found to drop precipitously thereafter with subsequent increase in degree of dehydration. Dehydration also causes cognitive impairment manifesting as, for example, delayed reaction times, delayed and impaired decision-making, and impaired memory and judgement. These effects can directly lead to an increased safety risk. If an individual's level of dehydration reaches critical levels, medical intervention is required to prevent permanent side effects or major vital organ failure. In the extreme cases, even death can occur. Because individuals do not have a way of effectively monitoring their hydration status during a workout, they often misunderstand how easily and quickly it can occur. Effects of dehydration in children, the elderly, and patients in critical care can be even more precipitated and/or damaging.

Managing hydration is complicated by a high degree of variability in sweat rates. Each individual can sweat at a different rate based on individual factors like age, gender, body mass, body fat percentage, and fitness level, among other factors. For any individual there are a number of additional variables that affect sweat rate from weather conditions, intensity of the physical activity, the amount and types of clothing or equipment worn, etc. The same individual can have different sweat rates for the same activity on any given day.

One method for measuring degree of hydration of is to record nude body mass before and after an activity. The difference in the before and after measurements is converted to a percentage body weight lost. Since this method for measuring dehydration can only be performed with measurements before and after an activity, individuals currently cannot determine their hydration status during the performance of the activity.

Other methods used to measure hydration status include collecting blood samples at regular intervals during activity and measuring the osmolality of the plasma with an osmometer. As current methods of collection of blood sample cannot be performed during an activity, this method has some of same problems as mentioned for nude body mass measurement method. It provides hydration status information before or after an activity, but not during. It is also prohibitively invasive and inconvenient. Similar to collecting blood for plasma osmolality measurement, available methods of collection of other bodily fluids for osmolality measurement as a way of determining hydration status is also used with less successful results. The other fluids collected include saliva, urine, sweat and tears. Each of these fluids presents challenges with both collection and osmolality measurement.

Some devices collect sweat with a patch that adheres to the skin. The sweat can either be collected into an absorbent patch or reservoir. The patch is then removed from the individual and osmolality of the sweat in the patch is measured with a benchtop device. A significant amount of sweat is required for this method; the individual must sweat for a minimum of 15 to 20 minutes to collect this minimum amount. This method cannot provide live, instantaneous hydration monitoring to the athlete. In addition, these patches need to be replaced every 15 to 20 minutes to be able to collect an accurate hydration status for the entire period of activity being studied. Thus, there exists a need for systems, devices, and methods for use in the near instantaneous measurement and analysis of body fluids A Sample Analysis System Embodiments described herein relate to systems, devices, and methods for use in the near instantaneous measurement and analysis of body fluids such as sweat and potential analytes contained therein. The disclosed embodiments of systems and devices are lightweight in nature and therefore can be worn by an individual during any form of activity. The disclosed systems, devices, and methods allow near instantaneous measurement and analysis of body fluids by their stand-alone, real-time nature of sample collection and analysis. The disclosed embodiments of systems and methods also support repeated instantaneous measurements of samples of bodily fluid, carried out over a period of time while the individual is engaged in the activity.

As used herein, the terms "analyte" and/or "target analyte" refer to any ion, molecule or compound to be detected and/or that can bind to a binding species (e.g., a detection molecule or reagent), as described herein. Suitable analytes can include but are not limited to, metal and non-metal ions (e.g., $Na^+$, $Cl^-$, $Ca^{2+}$, $K^+$, or $Mg^{2+}$ ions), nitrogenous compounds such as amino acids and urea, metabolites (e.g., lactates and pyruvates), xenobiotics such as drug molecules enzymes, metabolic by-products, disease related biomarkers, small chemical molecules such as, for example, environmental molecules, clinical molecules, chemicals, pollutants, and/or biomolecules. More specifically, such chemical molecules can include but are not limited to pesticides, insecticides, toxins, therapeutic and/or abused drugs, hormones, antibiotics, antibodies, organic materials, proteins (e.g., enzymes, immunoglobulins, and/or glycoproteins), nucleic acids (e.g., DNA and/or RNA), lipids, lectins, carbohydrates, whole cells (e.g., prokaryotic cells such as pathogenic bacteria and/or eukaryotic cells such as mammalian tumor cells), viruses, spores, polysaccharides, glycoproteins, metabolites, cofactors, nucleotides, polynucleotides, transition state analogs, inhibitors, nutrients, electrolytes, growth factors and other biomolecules and/or non-biomolecules, as well as fragments and combinations thereof. Some analytes described herein can be proteins such as enzymes, drugs, cells, antibodies, antigens, cellular membrane antigens, and/or receptors or their ligands (e.g., neural receptors or their ligands, hormonal receptors or their ligands, nutrient receptors or their ligands, and/or cell surface receptors or their ligands).

As used herein, the term "sample" refers to a composition that contains an analyte or analytes to be detected. A sample can be heterogeneous, containing a variety of components (e.g., different proteins) or homogenous, containing one component. In some instances, a sample can be naturally occurring, a biological material, and/or a man-made material. Furthermore, a sample can be in a native or denatured form. In some instances, processing may be performed on a sample prior to detecting an analyte. For example, a sample can be subjected to a lysing step, denaturation step, heating step, purification step, precipitation step, immunoprecipitation step, column chromatography step, centrifugation, etc. In some instances, separation and/or immobilization (via electrophoresis) of a sample can be performed on native substrates and/or an analyte of interest (e.g., a protein). In other instances, a sample can undergo denaturation to expose their internal hydrophobic groups for immobilizing in a fluid path.

As used in this specification and the claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used in this specification, the term "and/or" is used in this disclosure to mean either "and" or "or" unless indicated otherwise.

As used herein, "bodily fluid" can include any fluid obtained from a body of an individual (e.g., athlete, laborer, patient, etc.). For example, "bodily fluid" includes, but is not limited to, sweat, tears, blood, urine, breast milk, saliva, sebaceous fluid, mucus, vitreous, and the like, or any combination thereof.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 10% or less in either direction (greater than or less than) of the stated reference value unless otherwise stated or otherwise evident from the context (except where such number would exceed 100% of a possible value or fall below 0% of a possible value).

As used herein, the term "stiffness" is related to an object's resistance to deflection, deformation, and/or displacement that is produced by an applied force and is generally understood to be the opposite of the object's "flexibility." For example, a wall with greater stiffness is more resistant to deflection, deformation and/or displacement when exposed to a force than a wall having a lower stiffness. Similarly stated, an object having a higher stiffness can be characterized as being more rigid than an object having a lower stiffness. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

As used herein, the words "proximal" and "distal" refer to the direction closer to and away from, respectively, a user who would place the device or system against their body. Thus, for example, the end of a device first touching the body of the user would be the proximal end, while the opposite end of the device (e.g., the end of the device away from the body of the user) would be the distal end of the device.

As described in further detail herein, any of the systems, devices and methods can be used to collect and analyze bodily fluid samples in a repeated manner by, for example, collecting a first sample or a first volume of bodily fluid, testing that first volume or sample of the bodily fluid, expelling the first volume or sample of bodily fluid, and collecting a subsequent volume or sample of bodily after a given duration of time. Each of the terms "first," "subsequent" and/or "initial," can be used interchangeably to describe and/or refer to an amount, portion, or volume of bodily fluid that is collected, transferred, diverted, channeled and/or expelled during use of the sample analysis systems described herein. In some embodiments, the terms "first," "subsequent", and/or "initial" can refer to a predetermined, defined, desired, or given volume, portion, or amount of bodily fluid, that can depend on several parameters including device configuration, user needs, etc.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof.

The embodiments described herein and/or portions thereof can include components formed of one or more parts, features, structures, etc. When referring to such components it should be understood that the components can be formed by a singular part having any number of sections, layers, regions, portions, and/or characteristics, or can be formed by multiple parts or features. For example, when referring to a structure such as a wall or chamber, the structure can be considered as a single structure with multiple portions, or multiple, distinct substructures or the like coupled to form the structure. Thus, a monolithic structure can include, for example, a set of substructures. Such a set of substructures may include multiple portions that are either continuous or discontinuous from each other. A set of substructures can also be fabricated from multiple items or components that are produced separately and are later joined together (e.g., via a weld, an adhesive, or any suitable method).

A sample analysis system (also referred to herein as "SA system"), according to some embodiments, includes a one-time use or a single-use sample handling device and a durable, sample processing device that connects to the sample handling device. In some embodiments, the SA system includes a reusable sample handling device and a reusable durable sample processing device coupled to the sample handling device. The sample handling device is configured to collect a sample of bodily fluid, direct the sample to a testing and measurement interface, and allow testing of the sample with a test stimulus and measurement of a response signal from the sample in response to the test stimulus. After the testing of the collected sample, the sample handling device is configured to direct the sample to be expelled. The response signal can then be analyzed to determine quantitative properties of the sample, such as solute concentration, solvent content, analyte concentration, etc.

Sample Handling Device

FIG. 1 shows a schematic representation of a section of skin of a user and illustrates an example sample handling device positioned on the skin of the user. The schematic of the skin section shows a density of secretory glands (e.g., sweat glands) leading to pores that release a bodily fluid (e.g., sweat). The sample handing device (also referred to herein as "SH Device") is represented by a disc and shown to be positioned on the surface of the skin of a user. As shown, the disc is covering a subset of the pores releasing the bodily fluid and is configured to collect the sample bodily fluid (e.g., sweat) from the user that can be measured and analyzed while the user engages in an activity (i.e., in near real-time). Although the sample handling device is shown on the skin of the user for collecting and analyzing sweat, it should be understood that the sample analysis systems described herein including the sample handling device can be used without being attached to the user and can be used for analyzing any number of other bodily fluids.

Figure 2A:
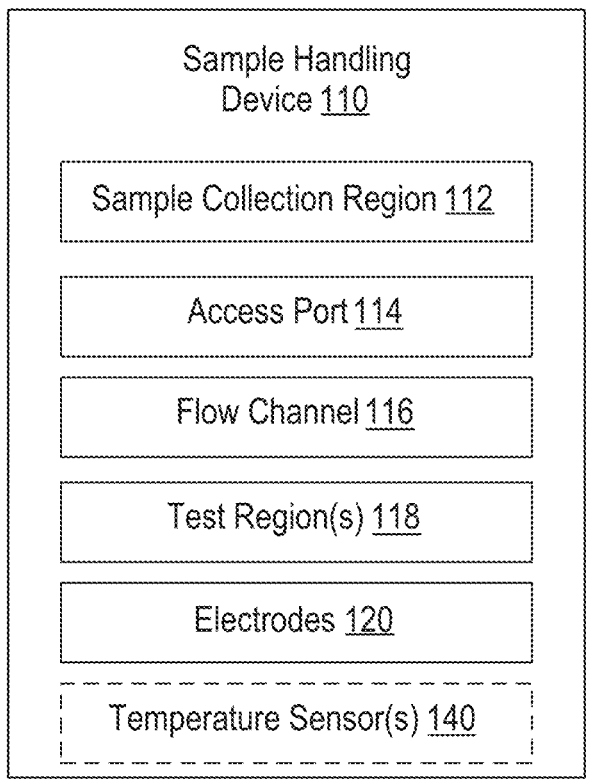
FIGS. 2A and 2B are schematic illustrations of a Sample Handling Device, according to an embodiment. The Sample Handling Device can be used with a Sample Analysis System ("SA system").
Figure 2B:
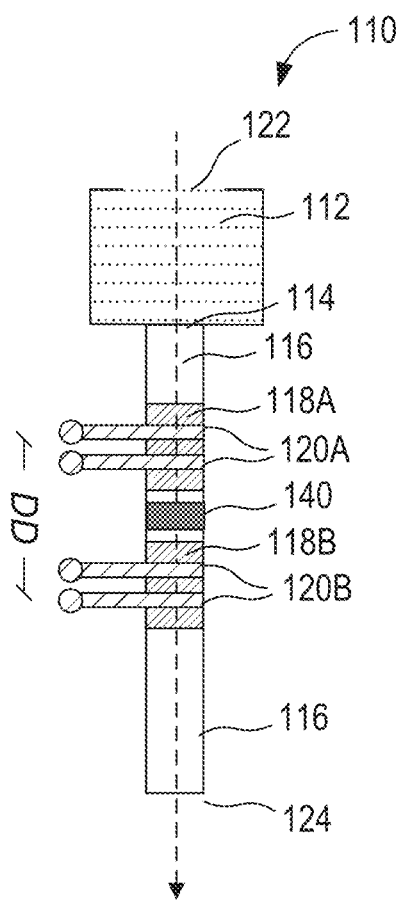

FIGS. 2A and 2B are schematic illustrations of an example sample handling device 110 indicating some components included in the sample handling device 110, according to an embodiment. Schematic in FIG. 2B includes an illustration of an example configuration of the various components of the sample handling device 110, and a flow path defined for the flow of a sample of bodily fluid indicated by the dashed arrow. In some embodiments, the sample handling device 110 can be constructed monolithically. In some other embodiments, the sample handling device 110 can be constructed through assembly of a set of portions or layers, as described in further detail herein. As shown in FIGS. 2A and 2B, the sample handling device 110 includes a sample collection region 112, an access port 114, a flow channel 116, test regions 118A, 118B, a set of electrodes 120A and 120B, and optionally a temperature sensor 140.

The sample collection region 112 is a portion of the sample handling device 110 that is configured to receive and collect a bodily fluid sample, for example sweat, from the body of a user when the sample handling device 110 is worn by the user. The sample collection device 112 includes an opening 122, indicated in FIG. 2B, that permits access to a source of bodily fluid when the sample handling device 110 is worn by a user. The sample collection region 112 also defines a space or volume configured to be fluidically coupled to the opening 122 and configured to hold or collect a sample of bodily fluid when the sample handling device 110 is worn by the user. While not shown in the FIGS. 2A and 2B, the sampling handling device 110 can include one or more interfacing structures between the user's body and the sample collection region 112 of the sample handling device 110. Such interfacing structures can be configured for ease of use or to increase comfort while using the sample handling device 110. For example, one or more liners can be used to provide a better interfacing with the user's body with increased comfort during use of the sample handling device 110. In addition, the interfacing structures can be used to provide a seal between the sample handling device 110 and the user's body such that pressure generated by the sweat glands urges sweat through the flow channel 116.

In some embodiments, the sample collection region 112 can be defined by one or more portions of the sample handling device 110. For example, in some embodiments, the sample collection region 112 can be formed by assembling two or more portions or layers of structures to include an opening 122 for collection of bodily fluid, and to define a specific volume to temporarily hold the collected sample of bodily fluid. The two or more portions or layers can be selected or made such that once assembled the sample collection region 112 includes a suitable opening 122 and the body of the assembled portion of the sample handling device 110 defines a volume in the sample collection region 112 that can hold a suitable amount of collected bodily fluid. For example, the thickness of two or more portions can be selected to determine the volume or fluid capacity of the sample collection region 112. The two or more portions can be assembled using any suitable method such as friction fitting, gluing using adhesive material (e.g., a transfer adhesive), using fasteners, etc. In some other embodiments, the sample collection region 112 can be formed monolithically by a single integral portion or structure, to include an opening 122 suitably configured to collect a sample of bodily fluid, and to define a volume to hold the collected sample of bodily fluid.

The portions forming the sample handle device 110 and/or the sample collection region 112 can have a suitable flexibility to provide ease of being worn by a user, and to provide ease of access to the source of bodily fluid. For example, in some embodiments the portions or layers forming the sample handling device 110 and/or the sample collection region 112 can be of flexible nature such that the sample handling device 110 can be worn on the surface of skin of a user and the proximal portion of the sample collection region 112 can optimally interface with the skin of the user and conform to the contours of the user's body, even when the user is engaged in activity. In some embodiments, the sample handling device 110 and/or the sample collection region 112 can have a relatively rigid construction such that the rigidity allows better interfacing with the surface of the user's body and prevents the sample handling device 110 from getting mispositioned or dislodged from the user during intense activity.

The opening 122 defined in the sample collection regions 112, shown in FIG. 2B, can be made accessible to a source of a sample of bodily fluid (e.g., skin containing sweat pores), and fluidically connected to the volume configured to temporarily contain the sample of bodily fluid collected from the source. The sample collection region 112 can be formed such that the volume and the opening 122 are defined in the body of the sample handling device 110, or a portion of the body of the sample handling device 110. In some embodiments, for example, the sample collection region 112 can be configured such that when the sample handling device 110 is positioned on the body of the user, the sample collection region 112 lies proximal to the surface of skin of the user and covers a suitable region of skin to collect a suitable volume of the bodily fluid such as sweat, over a suitable period of time. For example, as indicated in the schematic in FIG. 1, a section of human skin of a user can have a specific density of sweat pores that release sweat, each pore being spaced apart from the others at a specific distance. The sample collection region 112 can be configured such that the opening 122, when placed on the skin of the user, it can cover a certain area of skin containing a certain minimum number of sweat pores. Such a positioning can allow collection of an initial volume of sweat released from those pores over a desired period of time. In other words, the opening 122 can be sufficiently large to collect sweat from enough sweat glands to substantially fill the sample collection region 112 in a relatively short amount of time so the sweat can be analyzed shortly after the user starts perspiring.

In some embodiments, the SA system may require a minimum amount of bodily fluid for accurate testing and analysis. The opening 122 and/or the volume of the sample collection region 112 can be configured to determine the volume of bodily fluid collected in the initial sample, and to ensure that the collected initial sample satisfies the requirement of the minimum amount of fluid for accurate testing and analysis. In some implementations, the sample collection region 112 can include one or more structures (not shown in FIGS. 2A and 2B) configured to occupy and/or take up volume in the sample collection region 112 such that the volume of initial sample of bodily fluid to be collected and directed via the access port 114 can be smaller compared to the total volume defined by the sample collection region 112.

The space occupying structure(s) can be defined in the sample collection region 112, in any suitable manner. In some embodiments, the space occupying structure(s) can be solidly formed, for example using one or more spacer portions of spacer films to be assembled and/or deposited as material such as spacer ink (e.g., ink cured by ultraviolet light), or the like, on a surface of the sample collection region 112. For example, the space occupying structure can be included (e.g., deposited) on a layer or portion used to form a wall of the sample collection region 112. In some embodiments, the space occupying structures can be implemented by one or more spacer layers or portions assembled with one or more other portions to form the sample collection region 112. In some embodiments, the space occupying structure(s) can include an outer covering defining a hollow within and/or encapsulating a volume defined within the outer covering. In some embodiments, an outer covering of the space occupying structures can be molded and/or contoured to define a space that can be excluded or isolated from the volume defined by the sample collection region 112.

In some embodiments, the volume of the initial sample may also determine the ease of collection, direction of fluid flow to be tested, and expulsion, thereby determining the rate at which samples can be collected and tested or analyzed. Said in another way, in some embodiments of the sample handling device 110, an initial sample of bodily fluid (e.g., sweat) can be collected, the volume of the initial sample being determined by the volume of the sample collection region 112. The collected initial sample can be directed though the access port 114 into a flow channel 116 to be tested and expelled, in a continuous flow of bodily fluid, making room for continuous collection of bodily fluid subsequently secreted by the user during use. The processes of sample collection, sample testing and sample expulsion can be carried out in a continuous manner, with a continuous flow of collected bodily sample though the collection region 112, the access port 114, the flow channel 116, and the test region(s) 118, at a suitable rate. In such embodiments, the volume of the sample collection region 112 and the size of opening 122 defined in the sample collection region 112 can determine the rate at which the initial amount of sample is collected. The volume of the sample collection region 112 and the size of opening 122 can partially determine the linear flow rate (i.e., the volumetric flow rate divided by the cross section area of the flow channel 116) at which the sample is directed through the access port 114, the flow channel 116, and the test region(s) 118 before being expelled.

In some embodiments, as an example, the sample collection region 112 can have a volume and/or fluid capacity between about 0.001 milliliters (mL) and about 25.000 mL. In some embodiments, the sample collection region 112 can have a fluid capacity between about 0.001 mL and about 0.01 mL, between about 0.01 mL and about 0.50 mL, between about 0.01 mL and about 1.00 mL, between about 1.00 mL and about 25.000 mL inclusive of all ranges or subranges therebetween. In some embodiments, the sample collection region 112 can have a volume sufficient to house an initial amount of sample measured in volumes as small as a microliter (e.g., a volume as small as 0.001 mL of bodily fluid, 0.005 mL of bodily fluid, 0.01 mL of bodily fluid, 0.1 mL of bodily fluid, 1 mL of bodily fluid, 10 mL of bodily fluid, 25 mL of bodily fluid, 50 mL of bodily fluid or any suitable volume therebetween) or less of bodily fluid (e.g., a volume as small as 20 drops of bodily fluid, 10 drops of bodily fluid, 5 drops of bodily fluid, a single drop of bodily fluid, or any suitable volume therebetween). In other embodiments, the sample collection region 112 can have a volume up to, for example, about 5.0 mL, 10.0 mL, 15 mL, or more. In some embodiments, the sample collection region 112 can have a fluid capacity based on the volume defined by one or more space occupying structures and/or based on the volume isolated and/or removed by the space occupying structures, as described previously.

As shown in FIGS. 2A and 2B, the access port 114 of the sample handling device 110 is fluidically coupled to the sample collection region 112. The access port 114 can be an opening, a through hole, a conduit, a fluid flow path or the like, defined in the body of the sample handling device 110, to fluidically connect the sample collection region 112 to the flow channel 116, described in further detail below. In some embodiments, the sample collection region 112 can be formed by assembling two or more portions or structures, as described herein. In some embodiments, one of the portions can be configured to include and/or define the opening 122, while another portion can be configured to include and/or define the access port 114. One or more of the portions that are assembled can be configured to form, upon assembly, one or more walls of the sample collection region 112. In embodiments where the sample collection region 112 is defined in a monolithic structure, the access port 114 can be an orifice, a conduit and/or a flow path defined in the body of the sample handling device 110 to fluidically couple the sample collection region 112 with the flow channel 116.

The access port 114 can be situated at any suitable location with respect to the sample collection region 112 to mediate a fluidic connection between the sample collection region 112 and the flow channel 116. For example, in some embodiments the access port 112 can be an orifice defined on an inner surface of the sample collection region 112. In some embodiments, the access port 114 can be defined on a distal portion of the sample collection region 112 (i.e., away from the body of a user when the sample handling device 110 is in use). In some embodiments, for example, the access port 114 can be defined at a central portion with respect to the opening 122 and/or a volume defined by one or more walls of the sample collection region 112 to hold the collected bodily fluid. In some other embodiments, for example, the access port 114 can be defined in an off-center location with respect to the opening 122 and/or the volume defined by the walls of the sample collection region 112 to hold the collected bodily fluid. In some embodiments, the access port 114 can be located in any suitable position with respect to the sample collection region 112, the opening 122, and/or the flow channel 116 in order to prevent and/or flush formation of bubbles in the collected sample of bodily fluid. In some embodiments, the access port 114 can be situated at a position such that the sample collection region 112 is suitable formed to direct flow of fluid towards the access port 114, for example via a narrowing, conduit, contouring of one or more structures, and/or the like.

The access port 114 can be of any suitable size to allow transport of the collected sample of bodily fluid out of the sample collection region 112 to other portions of the sample handling device 110 (e.g., the test region(s) 118, etc.). In embodiments, the size of the access port 114 can be in the range of few hundred microns to few millimeters. For example, the access port 114 can have an internal, cross-sectional diameter between about 0.05 millimeters (mm) to about 5.0 millimeters (mm). In some embodiments, the access port 114 can have a cross-sectional area sufficient to permit continuous flow of collected sample of bodily fluid to the flow channel 116.

In some embodiments, the access port 114 can be configured to allow continuous flow of the collected sample of bodily fluid once the initial sample of the bodily fluid reaches a minimum amount in volume. In some embodiments, the access port 114 can be configured such that it permits a continuous flow of collected bodily fluid after the sample collection region 112 reaches a minimum amount of positive pressure from the collection of a substantial or minimum volume of bodily fluid (e.g., a volume as small as 20 drops of bodily fluid, 10 drops of bodily fluid, 5 drops of bodily fluid, a single drop of bodily fluid, 0.001 mL, 0.0015 mL, 0.010 mL, 0.05 mL, 0.2 mL, 1.00 mL, or any suitable volume therebetween).

The access port 114 can determine the rate of flow of collected bodily fluid to be tested using the SA system with the sample handling device 110. In some embodiments, the access port 114 can have wicking properties to draw the collected fluid sample from the sample collection region 112 into the flow channel 116. In some embodiments, the collected sample in the sample collection region 112 can be directed into the access port 114 and beyond by a pressure differential. For example, a lower pressure in the access port 114 and the flow channel 116 compared to the sample collection region 112 can draw the collected sample of bodily fluid through the access port 114 and the flow channel 116. Similarly, as the sample collection region 112 is increasingly filled with the collected bodily fluid, the increase in the pressure in the sample collection region 112 (i.e., generated by the sweat glands) can urge the collected sample of bodily fluid through the access port 114 into the flow channel 116. Said another way, the seal between the sample handling device 110 and the user's body is sufficiently fluid-tight such that pressure generated by the sweat glands urges sweat through the flow channel 116. In some other embodiments, the access port 114 can be configured such that the fluid in the sample collection region 112 is drawn out via capillary action.

The flow channel 116 can be of any suitable width, height, diameter, or cross-sectional area to receive the collected sample of bodily fluid from the sample collection region 112 via the access port 114 and to suitably transport the sample of bodily fluid to other parts of the sample handling device 110 such as the test region(s) 118. For example, the flow channel 116 can have a circular cross-section with a suitable diameter, or a rectangular cross-section with a suitable width and height of the flow channel 116. The width, height, or diameter of the flow channel 116 can be in the range of few hundred microns to few millimeters. For example, the width, height, and/or diameter of one or more portions of the flow channel 116 can be between about 0.05 millimeters (mm) and about 5.0 mm. The flow channel 116 can extend for any suitable length, from few millimeters to few centimeters, and be configured to assume any suitable shape along the length. For example, the flow channel 116 can extend over a length between 5 millimeters (mm) and about 15.0 centimeters (cm). The flow channel 116 can be configured to follow any suitable path such as a linear, rectilinear, curvilinear, or a serpentine path.

In some embodiments, the flow channel 116 can be formed to have a predetermined volume per unit length such that given a length of the flow channel 116 between any two points the volume of the portion of the flow channel 116 between those points can be calculated. For example, as shown in FIG. 2B, a flow channel 116 can include two test regions 118A and 118B with a spacing DD between them. Given the length DD of the flow channel 116 between two test regions 118, the volume of the portion of the flow channel 116 between the two test regions 118 can be calculated from which a volume of bodily fluid flowing between the two test regions 118 can be calculated. In some embodiments, the flow channel 116 can be formed such that the dimensions (e.g., height, width, diameter, length, etc.) of the flow channel 116 are within specified bounds of tolerance such that the volume of a portion of the flow channel 116 can be estimated within a specified degree of tolerance (e.g., within ±1 pL, ±1 nL±1 µL, etc.)

In some embodiments, based on the precision and/or tolerance in the dimensions of the flow channel 116, the SH device 110 can be configured such that, a delay in time between a portion of a sample of bodily fluid reaching the first test region 118A and the same portion of sample of bodily fluid reaching the second test region 118B can be measured. For example, the portion of the bodily fluid can be identified to first interact with the electrodes 120A at the first test region wherein a first excitation signal can be applied on the portion of bodily fluid and a response recorded. That same portion of the bodily fluid can then pass through the flow channel 116 of distance DD and the second test regions 118B wherein a second excitation signal can be applied, and the response evoked can be measured. Based on the responses measured at the first and second test regions 118 the portion of the bodily fluid identified at the first test region can be identified when passing through the second test region 118B, after a measured period of time T, as described in further detail herein. Based on the known volume of the portion of the flow channel 116 between the test regions 118A and 118B along the distance DD, and the measured time period T, a volumetric flow rate associated with the flow of the sample of bodily fluid can be calculated. In some instances, as described herein, the bodily fluid collected and analyzed can be in the form of a continuous flow of bodily fluid for a region of portions of a user's body (e.g., unimpeded flow of perspirations from a patch of skin on an arm/chest/abdomen/shoulder of a user). Thus, the calculated volumetric flow rate of the sample of bodily fluid can be used to generate an estimation of the rate of secretion or expression of the bodily fluid in the user's body at the localized portion of the user's body and/or the whole body of the user. While two test regions are described in the examples herein, in some embodiments, the SH device 110 can suitably include any number of test regions, for example, a third, fourth, and a fifth test region and so on.

In some embodiments, the flow channel 116 can be defined within an integral structure built monolithically such that the diameter of the flow channel 116 is determined at least partially by the thickness of the monolithic structure defining the flow channel 116. In some other embodiments, the flow channel 116 can be constructed by assembling two or more portions or layers of structures, collectively defining the flow channel 116. In some embodiments, the flow channel 116 can be formed by several layers or portions assembled together to direct flow of fluid via one or more channels, though holes, apertures, and/or the like. The flow channel 116 can be configured such that external influences during use such as forces arising from gravity, movement of a user's body, and the like, do not interfere with flow of fluid within the flow channel 116.

In some embodiments, the flow channel 116 can include various portions suitably configured to direct flow of bodily fluid with a suitable rate of flow or volume of flow. For example, in some embodiments, the flow channel 116 can include portions that are configured with different cross-sectional shape and/or size. For example, some portions of the flow channel 116 can be circular or rectangular while other portions are not. Similarly, some portions of the flow channel 116 can have a narrower or broader cross-sectional area compared to other portions of the flow channel 116. In some embodiments, the flow channel 116 can include an inflow portion and an outflow portion. The inflow portion of the flow channel 116 can be configured to transport bodily fluid collected in the sample collection region 112 to the test regions 118 described below via the access port 114. The outflow portion of the flow channel 116 can be configured to remove the sample of the bodily fluid, after testing at the test region(s) 118, to be expelled out of the sample handling device 110, for example to the environment. For example, in some embodiments, the flow path 116 can be configured to be linear at some portions defined by the one or more test regions 118 and the outflow portion of the flow channel 116 can include a tortuous vent path to reduce and/or avoid air ingress.

The inflow and outflow portions of the flow channel 116 can be suitably shaped to allow for optimal flow of the sample of bodily fluid, for optimal access to the sample of bodily fluid for testing, and for optimal expulsion of the sample after testing. In some embodiments, portions of the flow channel 116 may also include structural and/or functional adaptations to overcome or allow tolerance to physical forces such as stress and/or strain that may be encountered when the sample handling device 110 is used when the user engages in intense activity. For example, in some embodiments, the flow channel 116 can be configured to include suitable linear, angular and/or curved portions or serpentine portions to better tolerate different types of physical forces, including stress and/or strain encountered when the sample handling device 110 worn by a user during high-intensity or contact sport activities. In some embodiments, the flow channel 116 may be configured to include one or more curved portions or serpentine portions to acts as localized traps to prevent air from outside the sample handling device 110 to enter the flow channel 116.

As indicated in the schematic in FIG. 2B, the flow channel 116 can include an outlet 124 to expel the collected and tested sample of bodily fluid. In some embodiments, the sample of bodily fluid can be directed through the outflow portion of the flow channel 116 and via the outlet 124 by virtue of a sequence of pressure differentials. In some other embodiments, the sample of bodily fluid, after testing at the test region(s) 118, can be directed towards the outlet 124 by one or more suitable physical forces. For example, the sample of bodily fluid can be expelled via the outlet 124 by gravitational force, capillary action, motion of the user and/or the like.

As shown in FIGS. 2A and 2B, the sample handling device 110 incudes the test regions 118A and 118B. While illustrated as having two test regions 118A and 118B, in some other embodiments the sample handling device 110 can include any suitable number of test regions defined along the flow channel 116. For example, in some implementations, the sample handling device 110 can include one, two, three, or more test regions defined at specified portions of the flow channel 116 such that bodily fluid collected at the sample collection region 112 can be directed via the access port 114 and through one or more of the test regions for sequential or parallel processing, as described herein. In some embodiments, the test region(s) 118 can be separated from but fluidically coupled to the flow channel 116. In some embodiments, the test region(s) 118 can be defined as a portion of the flow channel 116. For example, the flow channel 116 can include the inflow portion and the outflow portion separated by the test region(s) 118 being a third portion. The test region(s) 118 can be configured to intersect with the flow of the bodily fluid in the flow channel 116. In some embodiments, the test region(s) 118 can be configured to define a volume sufficient to hold a portion of the sample of bodily fluid while being tested. As described previously, in some embodiments, the test regions 118A and 118B can be separated by a known distance DD which can be implemented to be within a specified tolerance during manufacture of the SH device 110.

The test region(s) 118 of the sample handling device 110 can include a set of electrodes 120. In some embodiments, the electrodes 120 can include electrodes configured to supply power to one or more components included in the sample handling device 110 (e.g., one or more sensors such as temperature sensors, etc.,) and/or to carry signals from the one or more components to a sample processing device (e.g., signals reporting temperature measurements by a temperature sensor).

The set of electrodes 120 can include excitation electrodes and sensing electrodes. In some embodiments, each electrode of the set of electrodes 120 can be configured to serve as either an excitation electrode or a sensing electrode. In some embodiments, the set of electrodes 120 can include excitation electrodes, designated to deliver excitation signals to a portion of a sample of bodily fluid at a test region(s) 118, and sensing electrodes designated to sense a response signal from the sample of bodily fluid in response to an application of an excitation signal. The set of electrodes can include a terminal end (indicated by circular portion of the electrodes 120A and 120B in FIG. 2B) configured to interact with a portion of a sample processing device described herein and a sample end configured to interact with a portion of sample fluid at one or more test regions 118.

In some embodiments, for example, an excitation electrode can be configured to receive, at a terminal end, an excitation signal from a source of electrical power and deliver, at the sample end, the excitation signal to the portion of the sample of bodily fluid directed with the flow channel and at the test regions 118. As another example, a sensing electrode can be configured to receive at a sample end interfacing with a portion of a sample of bodily fluid at the test regions 118, a response signal emitted from the sample portion of bodily fluid at the test regions 118 and deliver the received response signal to a terminal end interfaced with a portion of a sample processing device such that the response signal can be suitable processed and/or analyzed by a processor, and/or stored in a memory, associated with the sample processing device. In some embodiments, the sample processing device can be configured to receive response signals from electrodes 120 associated with two or more test regions 118A and 118B such that the response signal from each of the two or more test regions 118 can be compared to determine properties of the sample bodily fluid.

The set of electrodes 120 can include terminal ends that interface with a supply of electrical signals and/or power, for example at an electrical interface with a connector 125 for electrical coupling with a sample processing device 130, as described herein. The set of electrodes 120 can include sample ends formed to intersect with the flow channel 116 at one or more test regions 118 and configured to interface with the sample of bodily fluid flowing through the test region(s) 118. The set of electrodes 120 can include any suitable number of electrodes and the sample end of each electrode can be configured either to deliver an excitation signal to the sample of bodily fluid to be tested (e.g., as a current delivery electrodes), or to sense a response signal from the sample of bodily fluid tested with the excitation signal (e.g., as a voltage sensing electrode).

The number of electrodes can be suitably optimized in different embodiments of the sample handling device in consideration of parameters such as number of electrodes required for effective delivery of the excitation signal, number of electrodes required for a predetermined signal-to-noise ratio in the response signal obtained from the tested sample of bodily fluid, number of electrodes suitable to meet a predetermined form factor or structural and/or functional limitation, and/or the like. For example, in some embodiments the set of electrodes can include four electrodes, two of which are configured to deliver the excitation signal in the form of a test current signal, and two of which are allocated to record the response voltage from the sample of bodily fluid after applying the test current signal. As an example, the electrodes 120 can be configured as a four-pole impedance cell. As another example, in some other embodiments, the set of electrodes can include two electrodes, one configured to deliver the excitation signal and the other configured to read the voltage from the sample of bodily fluid being tested from which an impedance can be calculated. In some instances, the sensing electrode can be an impedance electrode configured to directly sense impedance in response to the application of an excitation signal for example application of a current. For example, the electrodes 120 can be configured as a bipolar impedance cell.

In some embodiments, one or more electrodes can be shared between multiple test regions. For example, in some embodiments, an excitation electrode configured to deliver current can be shared between two or more test regions 118 wherein the shared excitation electrode can have a single terminal end that interfaces with a connector 125 coupling to a sample processing device 130, and two or more sample ends disposed at the two or more test regions 118 (not shown in FIG. 2B).

In some instances, a distance between the electrodes 118 associated with the two or more test regions 118 can be used in the determination of properties of the sample bodily fluid. For example, an impedance associated with the response signal from each test region 118 can be used to assess a rate of flow and/or a rate of volumetric flow of the sample bodily fluid. In some instances, pattern recognition methods can be used to compare a first response (and/or impedance) measured at a first test region 118A from interaction with a portion of a bodily fluid with responses (and/or impedances) measured at subsequent test regions 118B to identify the same portion of the sample of bodily fluid evoking the first response. In some instances, a time delay between time of measuring the first response at the first test region 118A and the time of measuring subsequent responses at subsequent test regions 118B at known distances DD along the flow channel 116 can be used to determine a linear flow rate and/or a volumetric flow rate of the sample of bodily fluid using suitable methods and/or algorithms. From the volumetric flow rate of the sample bodily fluid a rate of secretion or expression of the sample bodily fluid (e.g., a rate a perspiration of sweat) can be estimated or extrapolated. In some embodiments, the excitation signal can be a test current signal used to test the electrodes 120 or other components of the SH device 110 and/or the sample analysis system the SH device 110 is included in (e.g., connectors, sample processing device, etc.)

In some embodiments, the electrodes 120 are configured such that the test current signal is in the form of direct current. In some embodiments, the electrodes are configured such that the applied test current signal is in the form of alternating current (AC). In the embodiments using alternating current, the electrodes 120 can be configured such that the alternating polarity of the test current signal experienced by the electrodes allows for partial reversal of the impact of the salinity of the sample of bodily fluid on the electrodes. Thus, the use of AC for excitation can aid in prevention of rapid corrosion or ionization of the electrical interface of the electrodes in the test region which may have otherwise been the result of a direct current excitation signal. In some embodiments, one or more of the electrodes 120 can have a carbon coating to reduce corrosive effects of the bodily fluids being tested. In some embodiments, the electrodes may be capacitively or AC coupled to the electronics such that no DC can flow through the sample, reducing the risk of corrosion or ionization.

In some embodiments, the electrodes 120 can be configured to detect a presence of one or more ions in the sample of bodily fluid. For example, in some embodiments, the electrodes 120 can be configured to detect the presence and/or quantify the amount of one or more of $Na^+$, $Cl^-$, $Ca^{2+}$, $K^+$, or $Mg^{2+}$ ions in the portion of the initial volume of bodily fluid.

In some embodiments, for example, the composition of the conductive ink used to form the electrodes (e.g., via screen-printing) may be optimized to perform specific detection and/or protection functions. In some embodiments, the electrodes may be coated with materials that can be used as binders for specific analytes that may be present in the sample bodily fluid to be analyzed. For example, the electrodes may be coated in specific functionalized material used to bind to and/or detect presence of the specific analytes, such that the presence and/or the concentration of the specific analytes may be determined. As an example, the coating be made using conductive ink which can be a silver/silver chloride alloy that is optimal for detection of ions. In some embodiments, different compositions of the conductive ink can be used to facilitate detection of specific targeted ions. In some embodiments, functionalized coatings can render the electrodes optimized for specific analytes, (e.g., $Na^+$) separately from other analytes (e.g., $K^+$, $Cl^-$, etc.). While described with reference to detect presence of ions, the systems, devices, and methods described herein can be equally suited and/or used to detect and/or quantify a presence of analytes in a sample of bodily fluid. For example, the presence of lactose, glucose, etc., can be detected and/or quantified.

In some embodiments, the sample handling device 110 can optionally include one or more temperature sensors 140. The temperature sensors 140 can be suitable located at or near the one or more test regions 118 and configured such that the temperature sensors 140 can record the temperature of the samples of bodily fluid being tested at the one or more test regions 118. In some implementations, the temperature sensors 140 can be positioned to monitor and measure the temperature of the sample of bodily fluid during testing in one or more test regions 118. The temperature sensor 140 can be any suitable temperature sensing device that can be suitably positioned adjacent to in suitable proximity to a test region 118 and used to measure a temperature of a sample of a bodily fluid. For example, the temperature sensor 140 can be a thermistor or a thermistor assembly. In some embodiments, the sample handling device 110 can include additional sensors (not shown) to record ambient conditions. For example, the sample handling device 110 can include temperature sensors to measure a temperature of a skin of a user and/or ambient air temperature. In some embodiments, the sample handling device 110, and/or the sample processing device coupled to it, can include any number of additional sensors to sense pressure, humidity, etc.

In use, the sample handling device 110 is positioned on the surface of the body of a user to collect and direct bodily fluid for testing and analysis, to determine a physical state of the user and/or his/her wellness. For example, the sample handling device 110 can be positioned on an arm of an athlete engaged in a sporting event to collect and test the user's sweat and analyze the collected sweat for its salinity from which the user's state of hydration, electrolyte losses, and perspiration rate can be determined. The sweat is collected in the sample collection region 112 of the sample handling device 110 and continuously directed through the access port 114 to the flow channel 116. In some instances, a spacer portion included in the sample collection region 112 can occupy space within the sample collection region 112 and reduce the amount of sample of bodily fluid required to be collected to urge or start the flow of bodily fluid via the flow channel 116. Portions of the flow channel 116 are configured to direct the collected sweat, at a continuous rate of flow, to the test region(s) 118 where the sweat interacts with the set of electrodes 120. An excitation or test current signal is delivered to the sample sweat in the test region(s) 118, via one or more electrodes (current delivery electrodes) from the set of electrodes 120. The response voltage generated by the sweat sample in response to the excitation or test current signal is read by one or more electrodes (voltage sensing electrodes, different from the current delivery electrodes), from the set of electrodes 120. In some instances, the excitation or test current signal can be delivered and the response voltage can be read in a continuous manner. The voltage read from the sweat sample is used to compute an impedance associated with the sweat sample, and the impedance can be correlated with a quantification or measure of salinity of the sweat as well as other physiological information of the user. Thus, the sweat of the user can be continuously tested over a period of time and the measure of salinity of the user's sweat can be correlated to a continuous measure of degree of hydration electrolyte losses, and perspiration rate of the user over the period of time while the user is engaged in an activity.

An Example Sample Analysis System

Figure 3:
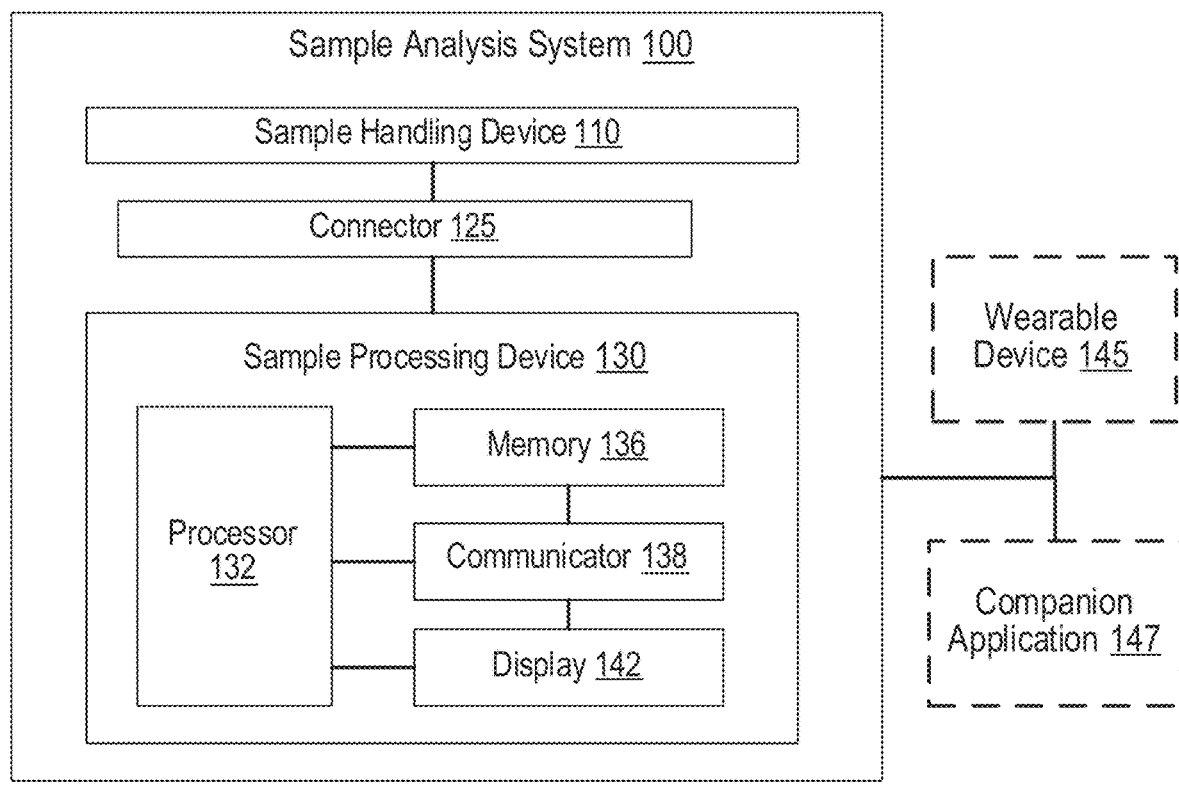
FIG. 3 is a schematic illustration of an example Sample Analysis System ("SA system") including the sample handling device of FIGS. 2A, 2B, according to an embodiment.

FIG. 3 is a schematic illustration of a Sample Analysis system 100, according to an embodiment. The SA system includes the sample handling device 110 (also referred to herein as the SH device) as described above, and a sample processing device 130, (also referred to herein as the SP device) coupled to each other via a connector 125. In some embodiments, the connector 125 can be permanently connected or removable from the sample handling device 110 and/or the sample processing device 130. In some instances, the sample analysis system 100 can be configured to incorporate a wearable device 145 (e.g., a smart watch, wristband odometer, activity tracker, heart rate monitor, and/or the like that may be commercially available (e.g., devices available from Garmin®, Fitbit®, Apple Watch®). While the SA system 100 is illustrated in FIG. 3 to include a sample processing device 130 and be coupled to a wearable device 145, in some implementations, the sample handling device 110 can be directly coupled to or connected to the wearable device 145 without requiring the sample processing device 130.

Figure 23:
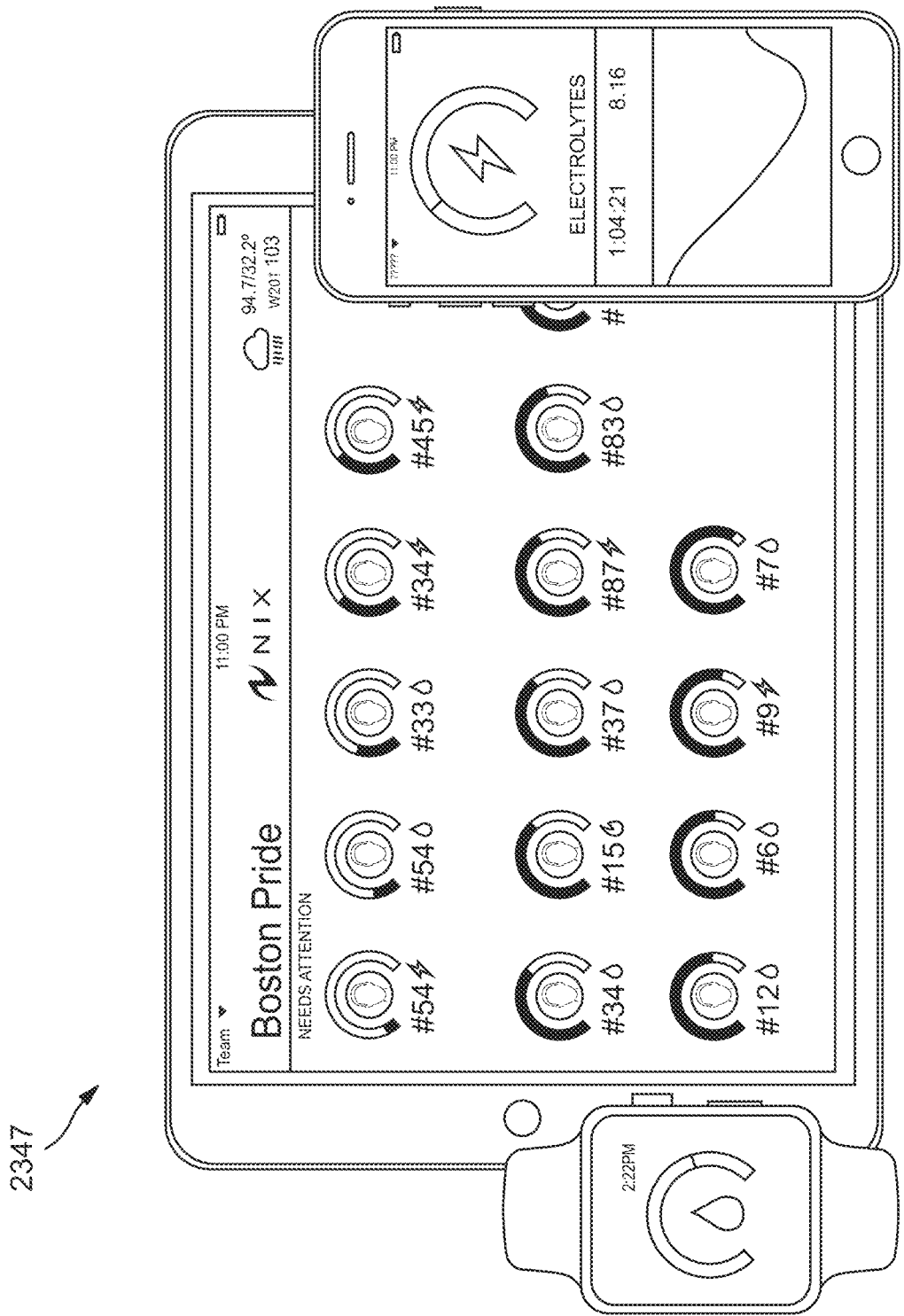
FIG. 23 shows an example illustration of a companion application used with a sample handling device, according to some embodiments.

In some implementation, the SA system 100 can optionally include and/or be configured to work with a companion application 147 that can be instructions stored in a memory and executed by a processor. In some embodiments, the companion application 147 can be executed in a remote device (e.g., a smart phone, tablet, computer, etc.). The companion application 147 can be configured to receive data from the SH device 110 and/or the sample processing device 130, and/or the optional wearable device 145 and perform additional analyses and/or generate data reports for a user. An example implementation of a companion application 147 is shown in FIG. 23.

The connector 125 can be a mechanical connector configured to engage, couple and/or connect the sample handling device 110 with the sample processing device 130. In some instances, the connector 125 can be configured to engage with portions of the sample handling device 110, such that the sample handling device 110 can be mounted on the sample processing device 130 before being worn by the user. In some embodiments, the sample processing device 130 can be configured to a durable multi-use device and the sample handling device 110 can be configured to be a single-use device that can be mounted and/or connected to the sample processing device for a period of use (e.g., an activity period) and discarded to be replaced by another sample handling device 110. The connector 125 can be configured such that it allows ease of removal and replacement of a sample handling device 110. In addition to a physical connection, the connector 125 can include a set of suitable electrical connections to electrically couple the sample handling device 110 to the sample processing device 130. For example, the connectors can be in the form of pogo pins or flexible contacts that can be engaged to provide an electrical connection upon the sample handling device 110 being mechanically coupled to the sample processing device 130, for example using a snap ring interface. While described to be configured to connect the sample handling device 110 with the sample processing device 130, in some embodiments, where the sample handling device 110 can be directly mounted onto a wearable device 145, the connector 125 can be configured to engage, couple and/or connect the sample handling device 110 with the wearable device 145.

The sample processing device 130 can be of a suitable form factor to be easily worn by a user when engaging in intense bouts of activity such that the sample handling device 110 can be appropriately interfaced with the body of the user (e.g., a portion of skin of the user). The sample processing device 130 can include a processor 132, a memory 136, a communicator 138, and a display 142.

The processor 132 can be, for example, a hardware based integrated circuit (IC) or any other suitable processing device configured to run and/or execute a set of instructions or code. For example, the processor 132 can be a general purpose processor, a microprocessor, a central processing unit (CPU), a microcontroller, an accelerated processing unit (APU), an application specific integrated circuit (ASIC), a field programmable gate array (FPGA), a programmable logic array (PLA), a complex programmable logic device (CPLD), a programmable logic controller (PLC) and/or the like. The processor 132 is operatively coupled to the memory 136 through a system bus (for example, address bus, data bus and/or control bus). The processor 132 can be configured to perform a set of functions to near-instantaneously or in real-time test, measure and analyze properties of the sample bodily fluid collected by the sample handling device. For example the processor 132 can be configured to generate a set of excitation signals to probe the sample of bodily fluid, to provide instructions on delivery of the excitation signals via the electrodes in the sample handling device 110, to receive the response signals obtained from the sample of bodily fluid read by the electrodes in the sample handling device 110, and to interpret the response signals to determine properties of the sample bodily fluid and by extension indicate a physical state of the user. In some embodiments, the processor 132 can also be configured to perform additional functions such as indicate to the user via a display 142 relevant information regarding the properties of the sample bodily fluid analyzed and/or a state of the user at the time of testing. The processor 132 may also be configured in some embodiments to transmit a set of signals, interpretations, and/or results of analyses to remote compute devices for further processing, as described herein.

The memory 136 of the sample processing device 130 can be, for example, a random-access memory (RAM), a memory buffer, a portable hard drive, a read-only memory (ROM), an erasable programmable read-only memory (EPROM), and/or the like. The memory 136 can store, for example, user date for later use/analysis and/or one or more software modules and/or code that can include instructions to cause the processor 132 to perform one or more processes, functions, and/or the like (e.g., the generation of excitation signals, delivery of test signals, reading and analyses of response signals, etc.) described herein. In some implementations, the memory 136 can be a portable memory (for example, a flash drive, a portable hard disk, and/or the like) that can be operatively coupled to the processor 132. In other instances, at least a portion of the memory can be remotely operatively coupled with the sample processing device 130. For example, a remote database server can be operatively coupled to the sample analysis system 100 via the sample processing device 130.

The communicator 138 can be a hardware device operatively coupled to the processor 132 and memory 136 and/or software stored in the memory 136 executed by the processor 132. The communicator 138 can be, for example, a compact network interface card (NIC), a Wi-Fi module, a Bluetooth® module, a radio frequency communication module, and/or any other suitable wired and/or wireless communication device. Furthermore, the communicator can include a switch, a router, a hub and/or any other network device. The communicator 138 can be configured to connect the sample processing device 130 to a communication network or one or more compute devices. In some instances, the communicator 138 can facilitate receiving and/or transmitting a file and/or a set of files through a communication network to the one or more compute devices (e.g., computers, smart phones, remote databases, servers, etc.).

The display 142 can be a low power module configured to indicate one or more results from the analyses of the samples of bodily fluid collected and tested by the sample analysis system 100. For example, the display 142 can be configured to have a set of backlit icons indicating a state of hydration of the user, or an indication for increased hydration of a user, or the like. In some embodiments, the display 142 can also be configured to include a status indicator related to the sample processing device 130 or the sample handling device 110. For example, the display 142 can be configured to alert the user that a sample handling device 110 needs to be changed or that a sample processing device 130 needs to be charged with power. For example, the sample processing device 130 can be configured to be powered by a disposable or re-chargeable battery power supply unit. In embodiments that include rechargeable power supply, the sample processing device 130 can include adaptations for re-charging the power supply unit when plugged to a power outlet. In some embodiments, the sample processing device 130 can include devices to indicate a state of charge.

Figure 4:
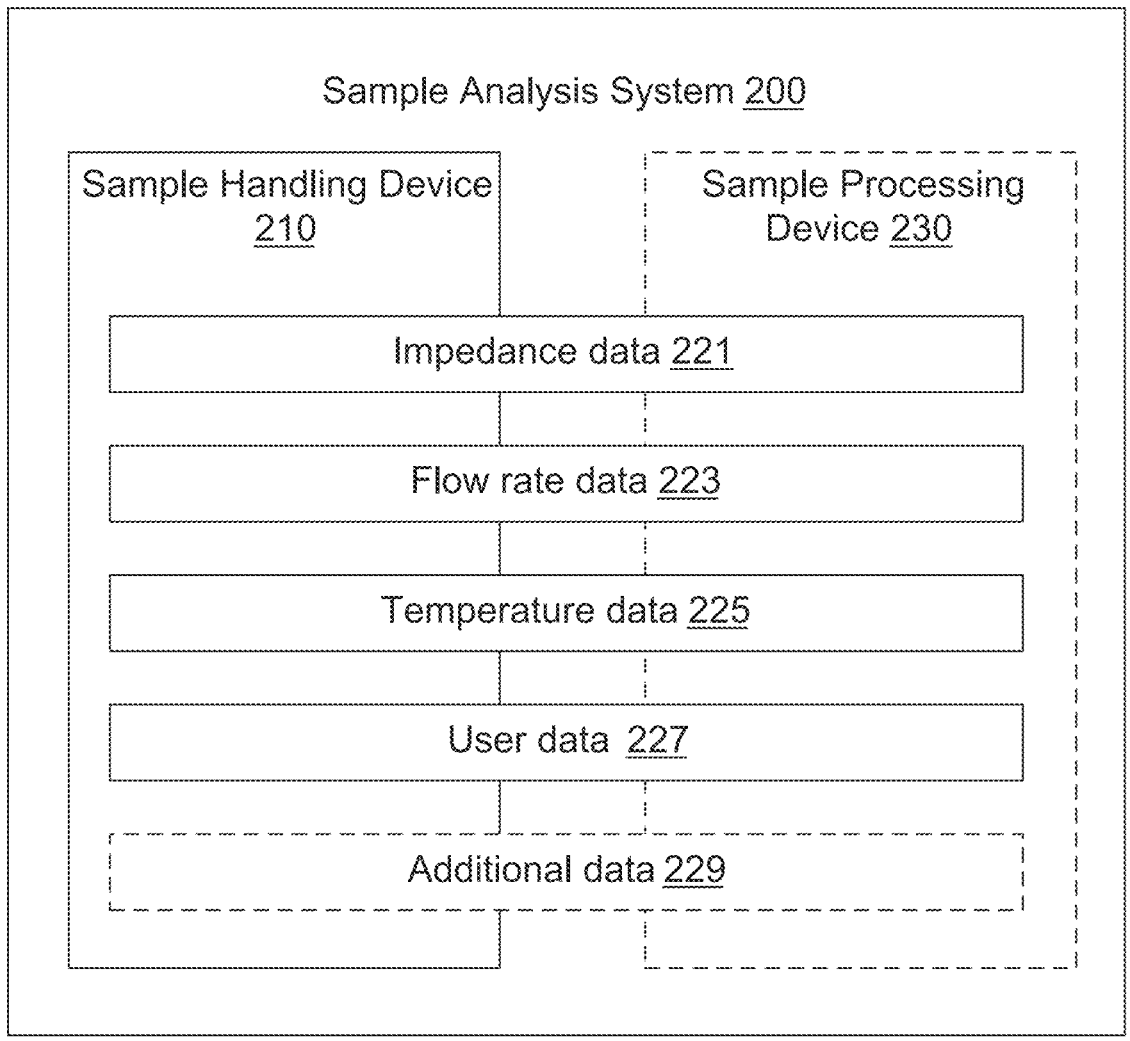
FIG. 4 is a schematic illustration of example data stored and/or used by a sample handling device, according to one embodiment.

FIG. 4 is a schematic representation of the different types of data handled by a sample analysis system 200, according to an embodiment. The sample analysis system 200 can be substantially similar in form and/or function to the sample analysis system 100 described above with reference to FIG. 3. For example, the sample analysis system 200 can include a sample handling device 210 substantially similar in form and/or function to the sample handling device 110 described with reference to FIGS. 2A and 2B. For example, the sample handling device 210 can include a sample collection region, an access port, a flow channel, a test region, and a set of electrodes, as described with reference to the sample handling device 110. The sample handling device 210 can be used to collect and analyze sample bodily fluids as described above with reference to the sample handling device 110. The sample analysis system 200 can optionally include a sample processing device 230 that is substantially similar in form and/or function to the sample processing device 130 described above. For example, the sample processing device 230 can include a processor, memory, communicator, and a display among other things. In some implementations, as described herein, the sample analysis system 200 can include a wearable device (not shown) or a remote device (not shown) operatively coupled to the sample handling system 210.

FIG. 4 illustrates the types of data used and/or stored by an example sample analysis system 200. The portions of the data described herein can be handled partially and/or completely by the sample handling device 210 and/or the sample processing device 230. For example, portions of data described herein may be stored, be used, and/or be sent from/received at the sample handling device 210 and/or the sample processing device 230 in any suitable manner. In some implementations, the data can be handled by one or more remote devices and/or wearable devices operatively coupled to the sample handling device 210 and/or the sample processing device 230. Data can include data collected, measured, and/or calculated by the sample handling device 210. Data can also include data obtained and/or calculated by the sample processing device 230. In some instances, data can also include data received by the sample analysis system 200 (e.g., data received from remote sources or external devices). In some implementations, data can include data collected, measured, and/or calculated by a companion application (not shown in FIG. 4), operatively connected to the SA system 200. The companion application (e.g., the companion application 147 described with reference to FIG. 3) can be configured to receive data from the SH device 210 and/or the SP device 230 and/or any remote devices/wearable devices coupled to or in use with SH device 210/SP device 230. The companion application can, for example, be configured to receive data, perform calculations, generate and/or report additional, downstream metrics (e.g., converting sweat losses into sweat rates, correlating it with weather, and/or user biometric information, and/or the like).

Impedance data 221 can include measurements of impedance from portions of sample fluids collected by the sample handling device 210 to be analyzed. In embodiments that include more than one test region the impedance data can include measurements of impedance at each test region.

In some instances, the measurements of impedance can be as a function of time. Flow rate data 223 includes data involved in calculation of flow rate of a sample bodily fluid analyzed by the sample handling device 210. In some implementations, the sample handling device 210 is configured such that measurements of impedance from two or more test regions can be used to estimate a flow rate associated with the sample bodily fluid being analyzed, as described herein. Temperature data 225 includes measurements of temperature of the sample bodily fluid during testing by the temperature sensor 140. In some instances, temperature data 225 can include temperature measurements by other temperature sensors associated with the sample analysis system 200. For example, in some instances, the temperature data 225 can include ambient temperature and/or body temperature of the user. In some instances, temperature data can include weather information received from external sources.

User data 227 includes any data associated with a specific user and or a subgroups or users. For example, in some embodiments, the sample analysis system 200 can be configured to collect and analyze bodily fluids from a user for a defined period of time at an instance of use. The sample analysis system 200 may then be reused by the same user for a second instance of use (e.g., with a different single-use sample handling device, or the same reusable sample handling device). The sample analysis system 200 may then be configured to track each use of the system by the same user. In some implementations, the SA system 200 can store user history associated with the user to be included in user data 227. User data 227 can also include information pertaining to one or more users including demographic information, personal information, identifying information, information indicating user preferences of use of the SA system 200, user activity profile, and/or the like.

The SA system 200 is configured to handle additional data 229 that can include data that is calculated and data that is used to perform the calculations. For example, additional data 229 can include data involved in the calculation of impedance, osmolality, hydration, fluid loss, electrolyte loss, sweat rate, core body temperature, etc. Additional data 229 can include data used for performing corrections of measured values based on other variables. For example, additional data 229 can include data used for temperature-based corrections of impedance measurements. Additional data 229 can include predictions made based on analyses of sample bodily fluids including prediction of fluid loss over an extended period of time, prediction of effects on the body, predictions or suggestions for hydration strategy, and the like. Additional data 229 can include data collected instantaneously or near instantaneously during use of a sample handling device 210 by a user (e.g., instantaneous flow rate, instantaneous state of hydration, etc.). Additional data 229 can also include cumulative data collected over a period of time (e.g., cumulative loss of fluids, cumulative loss of electrolytes, cumulative rates of loss of fluids and/or electrolytes, etc.)

Additional data 229 can also include analysis reports or summaries (e.g., post-activity summary). In some implementations, additional data 229 includes historical data pertaining to one or more users, geographical region of use etc. Additional data 229 can also include population data including statistical data, data related to social networks of users of SA systems, data used or obtained via a companion application used with a SA system, etc. In some implementations, additional data 229 includes product recommendations, performance indications, performance impairment measurements, proposed plans of recovery, etc.

Figure 5A:
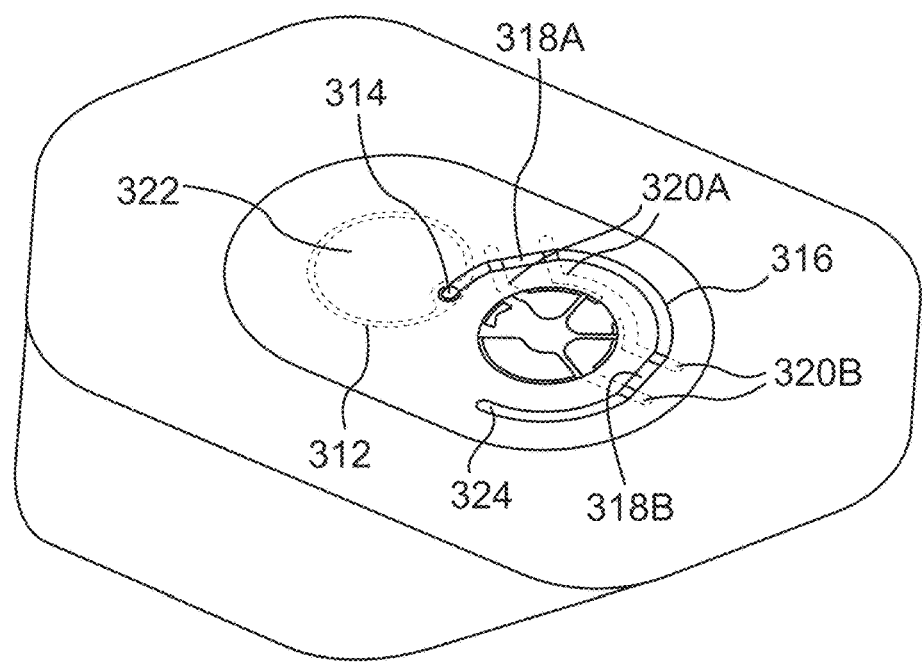
FIG. 5A is a schematic illustration of a perspective view of an example sample handling device, according to an embodiment.
Figure 5B:
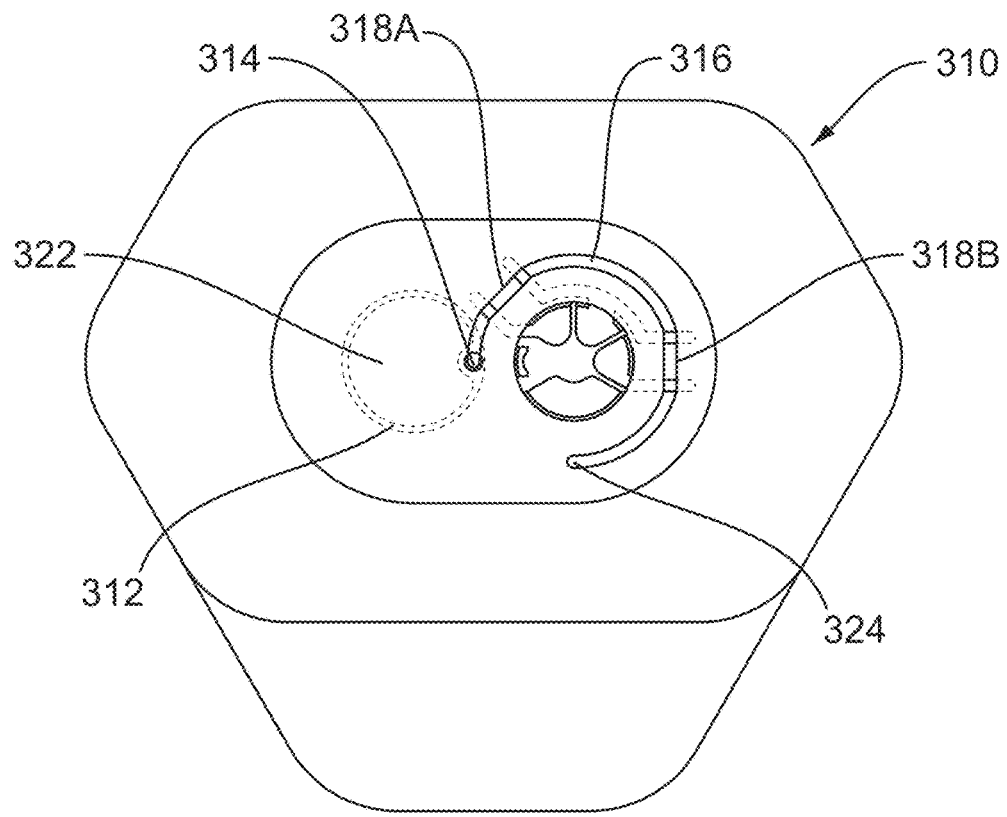
FIG. 5B is a schematic illustration of a top view of the example sample handling device in FIG. 5A.

FIGS. 5A and 5B illustrate an example sample handling device 310, according to an embodiment. The sample handling device 310 can be substantially similar in form and/or function to the sample handling devices 110 and 210 described above with reference to FIGS. 2A-2B, and 4 respectively. For example, the sample handling device 310 can include a sample collection region, an access port, a flow channel, a test region, and a set of electrodes, as described with reference to the sample handling device 110. The sample handling device 310 can be constructed in a manner that is substantially similar to the embodiments of the sample handling device described in the International Application No. PCT/US2019/061301, entitled "Wearable systems, devices, and methods for measurement and analysis of body fluids", filed Nov. 13, 2019, (the '301 application), the disclosure of which is hereby expressly incorporated by reference in its entirety for all purposes.

In some embodiments, a sample handling device 310 can be formed to include a series of test regions including a set of electrodes to test and evaluate optimal placement of test regions as shown in FIGS. 5A and 5B. Due to the specific placement of test regions 318A, 318B, and 318C and known separation between them, such an embodiment can be used to test a variety of distances to find the optimal distance between test regions.

Figure 5C:
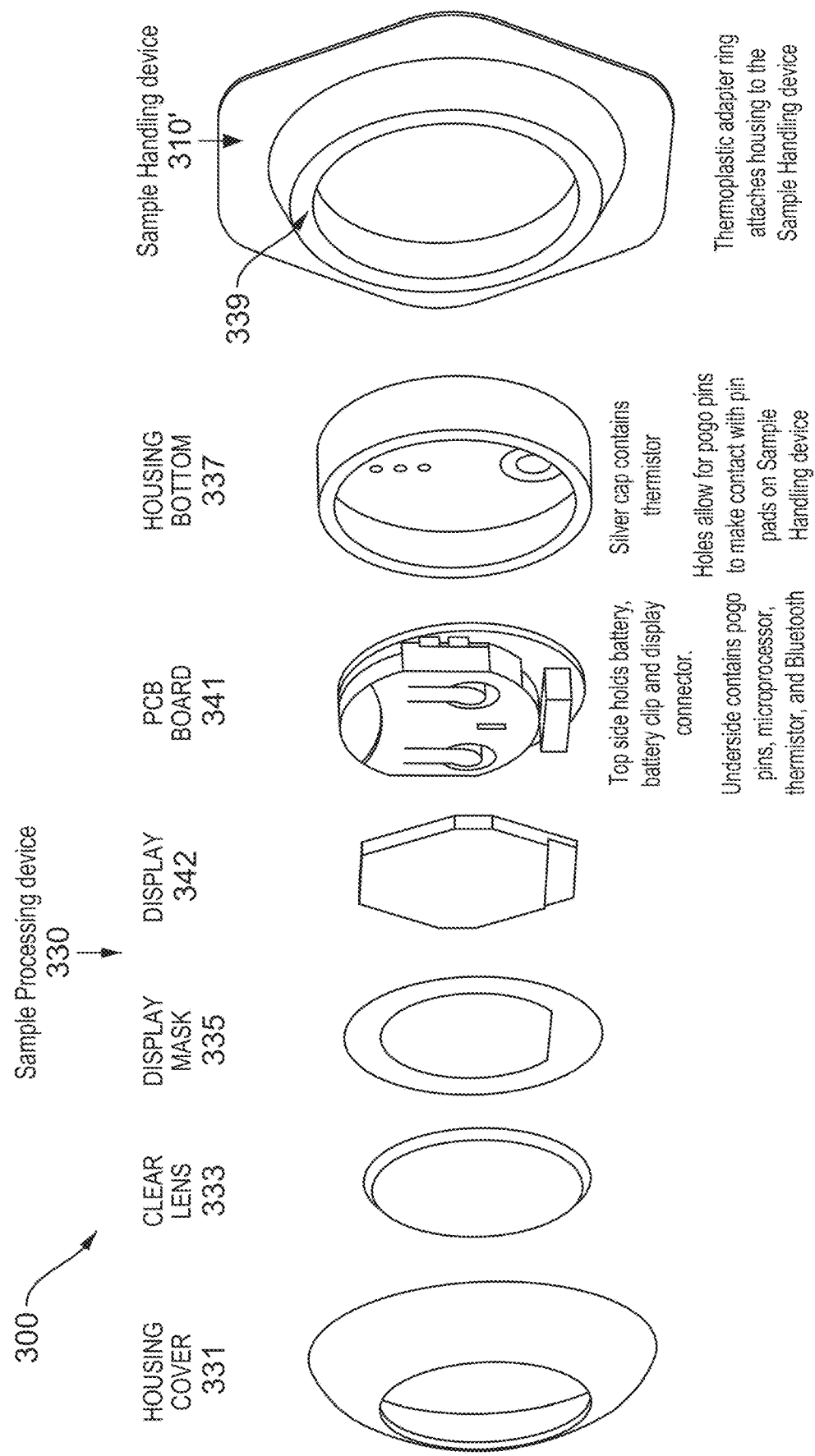
FIG. 5C is a schematic illustration of an exploded view of an example sample analysis system, according to an embodiment.

FIG. 5C illustrates an exploded view of an example sample analysis system 300 including a sample handling device 310', that can be substantially similar in structure and/or function to the sample handling device 310 described and show in FIGS. 5A and 5B. The sample analysis system 300 also includes a sample processing device 330, according to an embodiment. As shown, the sample processing device 330 includes a housing cover 331, a clear lens 333, a display mask 335, a display 342, a PCB board 341, a housing bottom 337, physical connectors 325, and electrical connectors (not shown in FIG. 5C) to connect to the sample handling device 310. The top side or the distal side (away from the sample handling device 310, and/or away from a user's body when system 300 is in use) of the PCB board 341 can be configured to hold a power source (e.g., battery) and a display connector. The proximal side (closer to the sample handling device 310, and/or closer to a user's body when the system 300 is in use) can include pogo pins serving as electrical connectors 325 between the sample processing device 330 and the sample handling device 310. The pogo pins (not shown) can interface with corresponding pin pads on the sample handling device 310 to make the electrical connections necessary to operatively couple the sample processing device 330 and the sample handling device 310 as described with reference to sample analysis systems 100, and/or 200 above. In some implementations, the system 300 can include a thermoplastic adaptor ring 339 as indicated in FIG. 5C, the adaptor ring 339 configured to attach the housing of the sample processing device 330 to the sample handling device 310.

Figure 6:
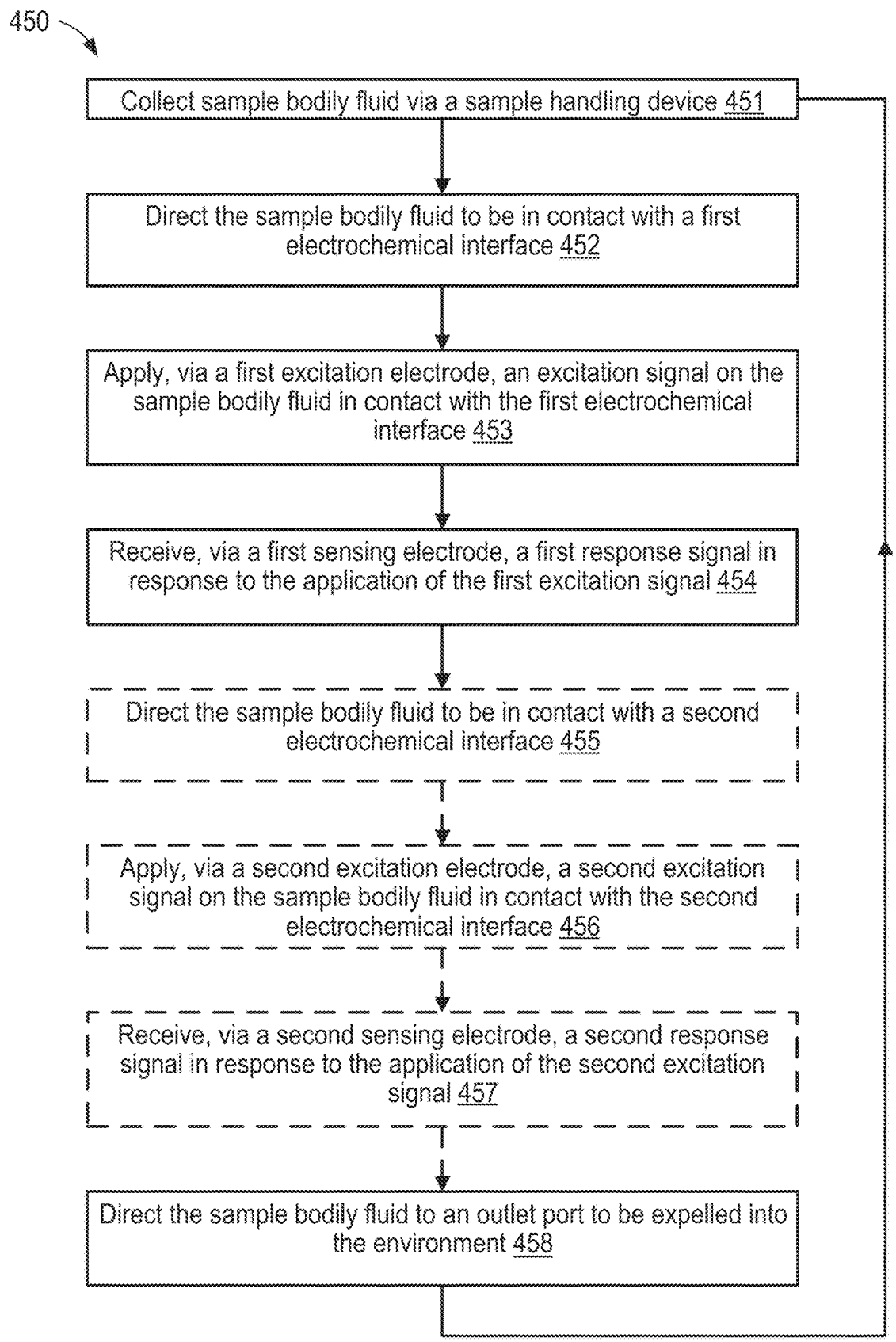
FIG. 6 is a flowchart schematically illustrating an example method of using a SA system to measure and analyze a sample bodily fluid from a user, according to an embodiment.

FIG. 6 shows a flowchart is shown illustrating a method 450 of using a sample analysis system including a sample handling device and a sample processing device, such as those described herein. The sample analysis system can be used to collect, test and analyze a sample of bodily fluid (e.g., sweat) at a near instantaneous, real-time rate and/or cumulatively over an extended period of time. In some embodiments, the sample analysis system can be similar to and/or substantially the same as any of the sample analysis systems 100, 200, and/or 300 working with any of the sample handling devices 110, 210, and/or 310 described herein.

The method 450 includes collecting a sample of a bodily fluid via a sample handling device of a sample analysis system, at 451. In some instances, for example, the bodily fluid source can be sweat. As the sample collection region of the sample handling device is filled to capacity or as a substantial amount of sample bodily fluid has been collected, the method includes, at 452, directing the sample bodily fluid to be in contact with a first electrochemical interface. In some instances, the collected sample is continuously directed towards the electrochemical interface, tested and expelled as new samples are continuously collected. For example, the sample fluid is directed through an access port via flow channel to a test region where the sample bodily fluid is made to come in contact with the test ends of a set of electrodes.

The method 450 includes, at 453, applying via a first excitation electrode, an excitation signal on the sample bodily fluid in contact with the first electrochemical interface. The excitation signal can be any suitable signal (e.g., a pulse of direct and/or alternating current) with any suitable set of parameters to define the excitation the signal (e.g., magnitude, polarity, duration, etc.). In some implementations, the excitation signal is delivered via the test ends of a set of current delivery electrodes included in the sample handling device of the sample analysis system being used. The method 450 further includes at 454, receiving via a first sensing electrode, a first response signal in response to the application of the first excitation signal. The sample analysis system can be configured to receive a response signal (e.g., a near instantaneous response signal), from the sample bodily fluid, after the application of the excitation signal. For example, the response voltage can be read via the test ends of a set of voltage sensing electrodes included in the sample handling device being used.

In some implementations, as described previously, two or more test regions can be included at a known separation along a flow channel in a sample handling device. The two or more electrochemical interfaces at two or more test regions can be used to obtaining responses from a portion of a sample of bodily fluid as the portion of sample bodily fluid is directed to flow along the flow channel, based on which flow rate estimations may be made. Accordingly, in some instances, the method 450 includes an optional set of steps 455-457 (indicated by the dashed lines) of directing and using an example second test region including a second excitation electrode and a second sensing electrode to obtain a second response signal from the portion of sample bodily fluid tested at the first electrochemical interface at the first test region.

At 455, the method 450 includes directing the sample bodily fluid to be in contact with a second electrochemical interface for example at a second test region. At 456, the method 450 includes applying via a second excitation electrode, a second excitation signal on the sample bodily fluid in contact with the second electrochemical interface. As described with reference to the first excitation signal, the second excitation signal can be any suitable signal (e.g., a pulse of direct and/or alternating current) with any suitable set of parameters to define the excitation signal (e.g., magnitude, polarity, duration, etc.). In some instances, the second excitation signal can be substantially similar to the first excitation signal (e.g., similar or same in magnitude, polarity, duration, etc.). In some implementations, the excitation signal is delivered via the test ends of a second set of current delivery electrodes included in the sample handling device of the sample analysis system being used.

At 457, the method includes receiving via a second sensing electrode a second response signal in response to the application of the second excitation signal at the second electrochemical interface.

In some implementations, one or more current delivery electrodes can be shared between two or more electrochemical interfaces at two or more test regions. For example, an excitation electrode with a single terminal end connecting to a source of the excitation signal (e.g., a terminal end in electrical communication with a portion of a sample processing device via an electrical connector) can have two sample or test ends that are situated at two electrochemical interfaces at two test regions. Thus, the shared excitation electrode can receive a single excitation signal from a sample processing device, for example, and apply the first excitation signal and the second excitation signal (which may be the same as the first excitation signal) simultaneously on portions of the sample bodily fluid at the first and second test region.

The first and/or the second excitation signal can be applied in a continuous manner while the sample bodily fluid is direct to flow through the flow channel of the sample handling device such that a given portion of the sample bodily fluid can be expected to pass through the first electrochemical interface at the first test region at a first time point and pass through the second electrochemical interface at the second test region at a second time point that occurs after the first time point by a specified duration or time delay.

The first and second response signals can be received and analyzed as a function of time. In some implementations, the first and second response signals may be analyzed in the time domain. In some instances, one or more algorithms (e.g., pattern recognition algorithms, template matching algorithms, and/or the like), may be employed to identify features in the first and second response as a function of time that can be used to determine the first time point at which a first response was obtained from a portion of sample bodily fluid at the first electrochemical interface (e.g., a first test region) and the second time point at which a second response was obtained from the same portion of sample bodily fluid at the second electrochemical interface (e.g., a second test region).

In some implementations, one or more statistical and/or analytical procedures may be conducted to identify the first and/or second responses associated with a portion of sample bodily fluid. In some instances, one or more procedures may be conducted using statistical and/or machine learning tools including neural networks (e.g., deep nets) that can be built either in association with a sample handling device or in association with a sample processing device. For example, procedures can include examining discrete time windows of the first and second response signals as a function of time. In some instances, the procedures can include calculating cross-correlations between identified time-windows of the first response signal with identified time windows of the second response signals. In some instances, a point of relative maximum in correlation values (e.g., a local maximum of correlation value) can be used to determine a relative shift between the first response signal and the second response signal based on which the time duration or time delay between the first time point and the second time point can be calculated.

In some implementations, the first and second response signals may be converted to phase space and analyzed for a maximum phase correspondence to identify the first and/or second responses associated with a specified portion of sample bodily fluid. In some implementations, conversion to phase space may be computation and/or time intensive. Thus, a sample analysis system can be configured to detect a state of use and based on the detected state of use select an appropriate method of calculation. For example, when a state of real-time use is detected, with limited time and/or processing power, a method of determining time-delay identified using maximum correlations may be employed. When a state of post-activity is detected and/or when time and/or processing power are not limited, a phase space-based calculation may be adopted.

In some implementations, based on the calculation of a volume associated with the known separation between the first electrochemical interface and the second electrochemical interface, and based on the calculated time duration or time delay between a portion of sample bodily fluid passing through the first electrochemical interface and the second electrochemical interface, a volumetric flow rate associated with the sample bodily fluid being analyzed can be estimated.

At 458, the method 450 includes directing the sample bodily fluid to an outlet port to be expelled in to the environment. In some implementations, the expelling of the sample bodily fluid can provide the impetus from flow of the bodily fluid remaining within the flow channel (e.g., via generating a pressure differential configured to draw more fluid towards the outlet port).

In some implementations, as described previously, the sample handling device of the sample analysis system can be configured to continuously collect and direct samples or volumes of the bodily fluid to the one or more test regions, test portions of the samples, and expel the samples to make room for the next sample. Thus, the method 450 can be carried out repeatedly for multiple samples providing intermittent or continuous results from testing and analysis, as indicated by the loop between steps 458 and 451 in method 450. The sample analysis system can be configured such that the time taken to collect a sample of bodily fluid sufficient for testing, time taken to direct the fluid to the test region and test the sample, and time taken to analyze the results of testing and expelling the sample can be reduced as required to suit the needs of the user. In some instances, adaptations of one or more parts of the sample handling device can be made to form a range of sample handling devices with varying response rates such that different users can obtain custom fitted or personalized sample analyses systems with personalized sample handling devices and/or personalized sample processing devices. In some embodiments, the data from different users (e.g., a team) can be stored, retained, and/or displayed to monitor the degree of hydration, electrolyte losses, and/or perspiration rate of the multiple users. In some instances, a user can choose a suitable sample analysis system based on the kind of activity they may engage or and the amount or rate of sample analysis they may desire.

For example, a user with a history of higher perspiration can use a sample handling device that includes a sample collection region with a suitably smaller opening to cover a smaller fraction of sweat glands compared to the sample handling device used by a user with very little perspiration. In some instances, a high-performance athlete requiring higher rates of sample analysis can use a sample handling device with a sample collection region of smaller fluid capacity such that smaller amounts of sweat are tested more frequently when the high-performance athlete user is using the sample analysis system when engaged in activities.

In some instances, the sample processing device can be personalized to store and retain history of results from analysis of a user's physical state or wellness for future uses of the sample analysis system. In some embodiments, the sample analysis system can be configured to export a set of collected data and/or analyses from the memory of the sample processing device to a remote device after predetermined, intermittent, periods. For example, in some implementations the sample analysis system may export data and/or results of analyses to a wearable device or a smart phone at every change or replacement of the sample handling device. In some embodiments, the exported data can be retained and logged, and associated with suitable identifiers tagged to users. The data associated with users can then be used to chart a progress of a user's physical state, wellness, performance or the like, and in some instances to predict physical/wellness states for individual users before they undertake planned activities. In some implementations the sample analysis system can include remote applications run on remote servers or compute devices to provide a plan for a user, for example a hydration strategy that might best suit a user such as a performance athlete when planning to undertake a pivotal sporting event. The remote applications can include prediction algorithms that can be used to devise strategic plans to hydrate, maintain electrolyte balance, and the like.

As described previously, the sample analysis systems and/or the sample handling device described herein can be integrated with wearable devices such as smart watches, odometers, GPS systems, etc. In some instances, when the sample analysis system including a sample processing device is integrated with the wearable device, the sample processing device can include interfacing elements to physically and electrically connect with the sample handling device. The sample processing device can perform functions such as provide instructions about delivery of an excitation signal, provide the excitation signal in the form of test current to the terminals of the electrodes, receive a response signal obtained via the electrodes from the sample being tested. The sample processing device can include the electronics required to analyze the response signal and/or communicate the data to remote compute devices, etc. For example, the electronics can be programmed with unique analytical code to interpret the readings collected. The interpreted readings can be output to the display of the sample processing device to provide the wearer with information about sweat rate and overall hydration status. In instances where the sample handling device can be directly interfaced with the wearable device, the wearable device can be configured to directly engage physically and electrically with the sample handling device and perform functions like providing instruction, providing the excitation signal, receiving and analyzing the response signal, etc. The electronics included in the wearable device can be used to execute programs with a unique analytical code to interpret the readings collected. The interpreted readings can be output to the display of the wearable device or a display associated with a remote compute device (e.g., a smart phone) to provide the wearer with information about sweat rate and overall hydration status.

Figure 7:
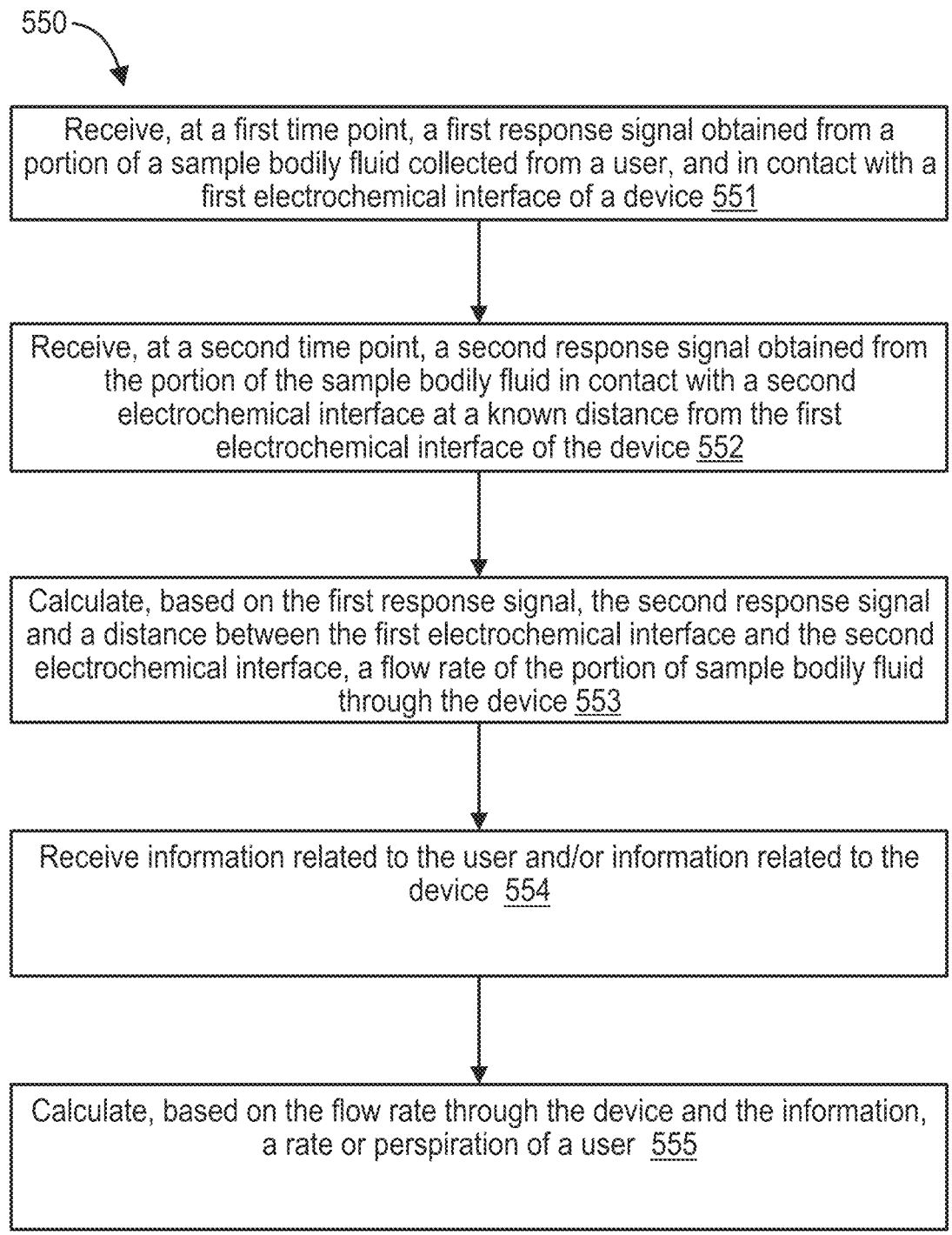
FIG. 7 is a flowchart schematically illustrating an example method of using a SA system to measure a rate of perspiration of a user, according to an embodiment.

FIG. 7 is a flowchart describing an example method 550 to calculate a rate of perspiration of a user using a sample handling device, according to an embodiment. The method 550 includes, at 551, receiving a first response signal obtained at a first time point from a sample bodily fluid collected from a user, and in contact with a first electrochemical interface of a device (e.g., a sample handling device 110, 210, and/or 310). The method 550 includes at 552, receiving a second response signal obtained, at a second time point, from the sample bodily fluid in contact with a second electrochemical interface at a known distance from the first electrochemical interface of the device. The second time point can be after the first time point. As described previously with reference to the method 450 above, the first response signal and the second response signal can be obtained in response to application of a first excitation signal at the first electrochemical interface and an application of a second excitation signal at the second electrochemical interface, respectively.

At 553, the method 550 includes calculating, based on the first response signal, the second response signal and the known distance, a flow rate of the sample bodily fluid through the sample handling device. For example, a linear flow rate can be calculated by estimating the time delay between a portion of the sample bodily fluid passing through the first electrochemical interface at the first test region and the same portion of the sample bodily fluid as determined by pattern recognition, template matching, determining maximum cross-correlation in time domain signals, determining maximum phase correlation in phase space, and/or the like as described above). A volumetric flow rate can be calculated by applying the known volume of the portion of the flow channel thought which the sample of bodily fluid is passing through, to the time duration or time delay calculated between responses received at the first electrochemical interface from the first test region and the corresponding second response signals received at the second electrochemical interface at the second test region. In some instances, the measured flow rate can be validated against known volumetric flow rate via the use of a calibrated syringe pump. In some implementations, the flow rate of portion of the sample bodily fluid that is calculated can be used to determine a local rate of expression or secretion of the bodily fluid at a portion of a user's body. For example, in some instances, the calculated flow rate of portion of the sample bodily fluid can be used to determine a local rate of perspiration of a user's body at a portion where the device is worn by the user (e.g., an arm, chest, abdomen, and/or the like). For example, a known value of the size of an opening (e.g., opening 122), size of access port (e.g., access port 114), size of sample collection region (e.g., sample collection region 112), and/or a size of flow channel (e.g., flow channel 116) of the SH device being used can be used to extrapolate from the calculated flow rate of portion of the sample bodily fluid to determine a local rate of perspiration of a user's body at a portion where the device is worn by the user.

In some instances, the method 550 includes at 554, receiving information related to the user and/or information related to the device. The information related to the user can include, for example, biometric/biographic data associated with the user (e.g., height, weight, BMI, gender, age, race, etc.). In some instances, the information related to the user can include, for example, physiological data including heart rate, breathing rate, temperature, etc. In some instances, the information related to the user can include, geographical location of user's activity, altitude, air pressure, ambient weather conditions, seasonal variations, etc.) The information related to the device can include information such as the collection parameters associated with the SH device being used (e.g., dimensions associated with the sample collection region, dimensions associated with the access port, manufacturing information associated with the device (e.g., device type (e.g., disposable/reusable) model, batch, identifying markers, and/or the like) usage of the device (e.g., time of use, duration of use, and/or the like).

At 555, the method 550 incudes calculating based on the flow rate through the device and the information, a rate or perspiration of a user. For example, based on the information related to the device (e.g., collection volume, area over which bodily fluid is collected, region of body over which sample handling device is placed to collect bodily fluid etc.,) and based on the calculated flow rate of bodily fluid through the sample handling device, a localized secretion or expression rate of the bodily fluid can be calculated. The localized secretion rate can be associated with the portion of body that the device is worn (e.g., forearm, upper arm, back of the hand, chest, back, abdomen, etc.)

As an example, based on the flow rate of collected sweat in a sample handling device, and based on an area defined by the inlet port and/or size (e.g., 12 mm diameter) and/or volume of the collection region of the sample handling device, a local sweat rate also referred to herein as local rate of perspiration, can be calculated for the portion of the body of the user from which sweat is collected during use. In some implementations, the local fluid loss information can be used to extrapolate to the full body rate of perspiration of the user. Based on information related to the user (e.g., body surface of the user, height, weight, race, ethnicity, diet, fitness, and/or the like) the local rate of perspiration can be extrapolated to obtain a whole body sweat rate of whole-body rate of perspiration. In some instances, the measured whole-body rate of perspiration can be validated against known methods of estimating rates of perspiration (e.g., via using Macroduct® Technology) via the use of a calibrated syringe pump.

In some instances, user behavior information (e.g., activity, pace of activity, intensity of activity, percentage of effort involved, $VO_2$ max, etc.) to calculate changes associated with full-body perspiration rate over the course of the activity (e.g., sweat rate variations with changes in intensity, effort, etc.,). In some implementations, further calculations can be made using full body perspiration and other related data obtained from additional sources. For example, environmental information (e.g., heat, humidity, cloud cover, wind, altitude, etc.) can be obtained from one or more sources (e.g., remote devices, wearable devices, etc.,) and based on the full body perspiration and the environmental information, an SA system can be used to calculate changes in full body sweat rate with environmental factors and variations thereof. In some implementations, the methods and/or systems described herein can be used to generate predictive models that can be used to provide predictive and/or anticipatory guidance to a user. As an example, in some implementations, full body perspiration rate, core body temperature, behavior information, and environmental information can be used to calculate the user's sensitivity to these factors and create a sensitivity model of the user's sweat rate based on these variables. The information and calculated values can be used to generate a predictive model of full body perspiration rate for that individual user in a future predicted location, based on predicted environmental information (e.g., temperature, humidity, altitude, wind, cloud cover, etc.) for a predicted duration and an intensity of their activity.

Figure 8:
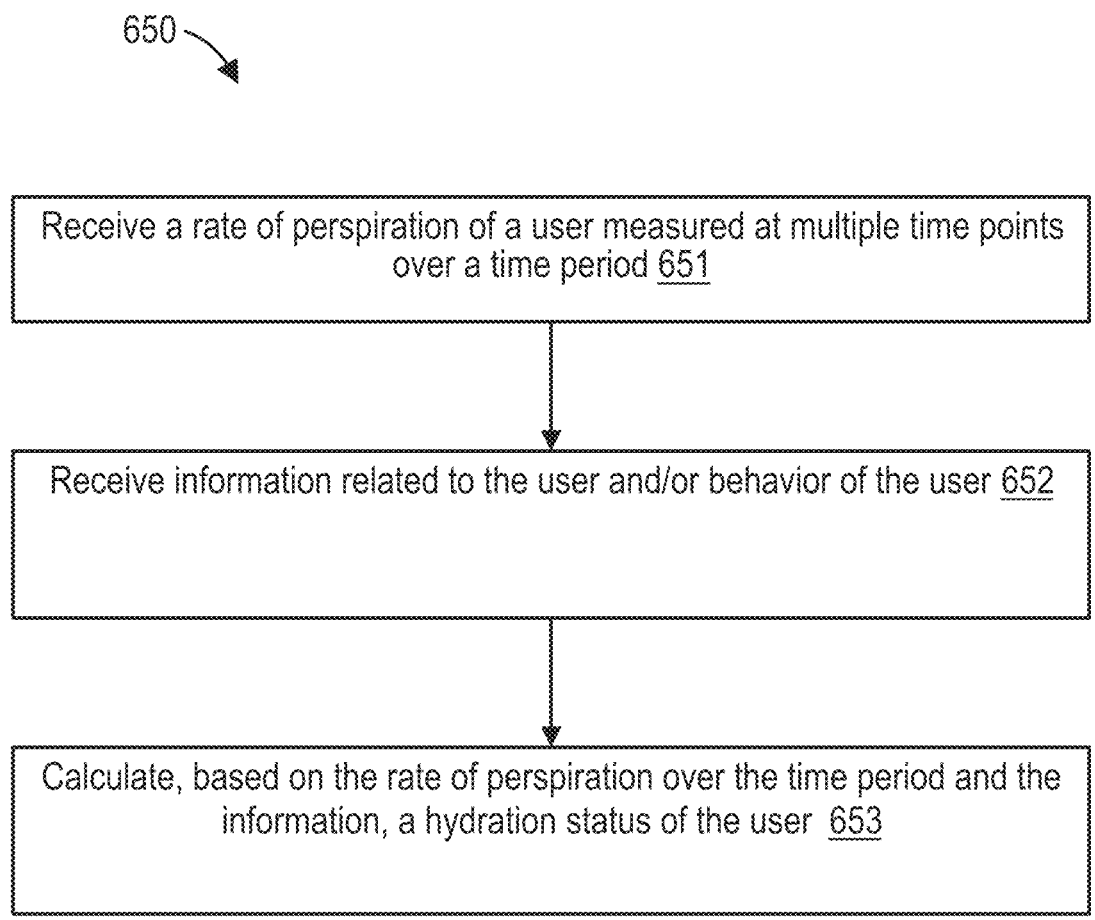
FIG. 8 is a flowchart schematically illustrating an example method of using a SA system to measure a hydration status of a user, according to an embodiment.

FIG. 8 is a flowchart describing an example method 650 to estimate a hydration status of a user using a sample handling device, according to an embodiment. The method 650 includes, at 651, receiving a whole-body rate of perspiration of a user measured at multiple time points over a time period. The rate of perspiration can be a whole-body rate of perspiration measured using method 450 and/or method 550 described in FIGS. 6 and 7, respectively. The method 650 further includes, at 652, receiving information related to the user and/or behavior of the user. For example, the information related to the user can include biometric, biographic, and/or physiological information. An example of information related to behavior can include information related to a starting body mass of the user and/or fluid intake of the user over the period of measurement of whole-body rate of perspiration. At 653, the method includes calculating, based on the whole-body rate of perspiration over the time period and the information related to physiology and/or behavior of the user, a hydration status of the user for the time period. For example, based on the measurements of whole-body rate of perspiration over a specified period of time a sample analysis system can calculate cumulative fluid losses incurred by the user. In some implementations, cumulative fluid losses can be estimated from calculating a time integral of whole-body rate of perspiration considered as a function of time over the specified period of time. In some instances, calculations of cumulative fluid losses suffered by a user can be validated by other independent methods such as by measuring changes in body mass from the beginning to the end of the specified period of time. The measured cumulative fluid loss over the period of time can be taken together with starting body mass of the user and by accounting for any intake of fluid during the specified period a net hydration status of the user can be estimated as a percentage change in body mass.

Figure 9:
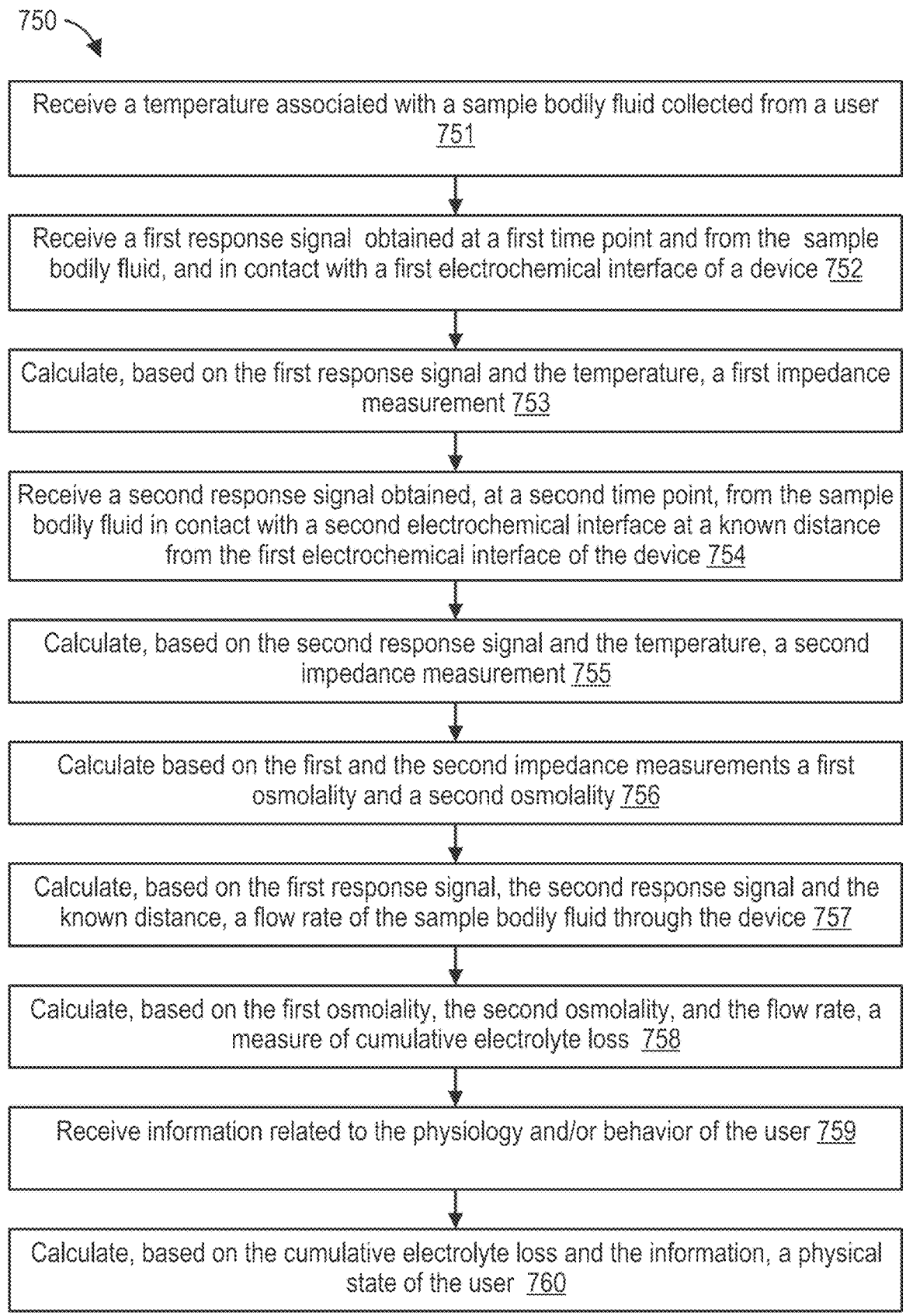
FIG. 9 is a flowchart schematically illustrating an example method of using a SA system to measure cumulative electrolyte loss and its associated physiological effects of a user, according to an embodiment.

In some implementations, measurements of impedance can be sensitive to temperature. It may be desired to correct or adjust impedance measurements taken from sample bodily fluids using sample handling devices described herein. FIG. 9 is a flowchart describing an example method 750 to estimate a temperature—adjusted measurement of impedance using a sample handling device, according to an embodiment.

At 751, the method 750 incudes receiving a temperature associated with a sample bodily fluid collected from a user. At 752, the method includes receiving a first response signal obtained at a first time point and from the sample bodily fluid, and in contact with a first electrochemical interface of a device. The temperature can be a temperature measurement associated with a user (e.g., skin temperature) made using a temperature sensor associated with a sample handling device (e.g., temperature sensor 140 of sample handling device 110) during measurement of impedance associated with a sample bodily fluid at an electrochemical interface of the sample handling device, as described herein.

At 753, the method 750 includes calculate, based on the first response signal and the temperature, a first impedance measurement. The first impedance measurement can be corrected for temperature using suitable temperature-based correction algorithms adapted to determine the amount of correction. In some instances, the impedance measurements and/or the temperature corrected impedance measurements can be validated using test runs involving blinded temperature sweep studies with impedance measurements made using independent methods for example using fixed resistors.

At 754, the method 750 includes receiving a second response signal obtained, at a second time point, from the sample bodily fluid in contact with a second electrochemical interface at a known distance from the first electrochemical interface of the device. At 755, as described previously with reference to the first response signal, the method involves calculating, based on the second response signal and the temperature, a second impedance measurement. The second impedance measurement can be a temperature corrected measurement using the temperature-based correction algorithms described above.

At 756, the method 750 includes calculating, based on the first and the second impedance measurements corrected for temperature, a first osmolality and a second osmolality. In some implementations, the sample analysis system can be configured to generate correlation curves that can be used to produce algorithmic formulae to convert temperature-corrected impedance measurements to osmolality.

At 757, the method 750 includes calculating, based on the first response signal, the second response signal and the known distance, a flow rate of the sample bodily fluid through the device. The calculating of flow rate can be similar to methods 450 and/or 550 described above. At 758, the method involves calculating, based on the first osmolality, the second osmolality, and the flow rate, a measure of cumulative electrolyte loss. The measurement of cumulative electrolyte loss can be based on method of measuring cumulative fluid loss as described by methods 550 and/or 650. For example, flow rate of a sample bodily fluid and instantaneous electrolyte loss over a period of time can be used to calculate a cumulative electrolyte loss which can be defined by the time integral of instantaneous electrolyte loss.

As described previously, at 759, the sample analysis system may receive information related to the physiology and/or behavior of the user, and at 760, the method includes calculating, based on the cumulative electrolyte loss and the information, a physical state/wellness of the user. In some instances, the method 750 includes calculating, based on the cumulative electrolyte loss and the information, a state of wellness of the user.

Figure 10:
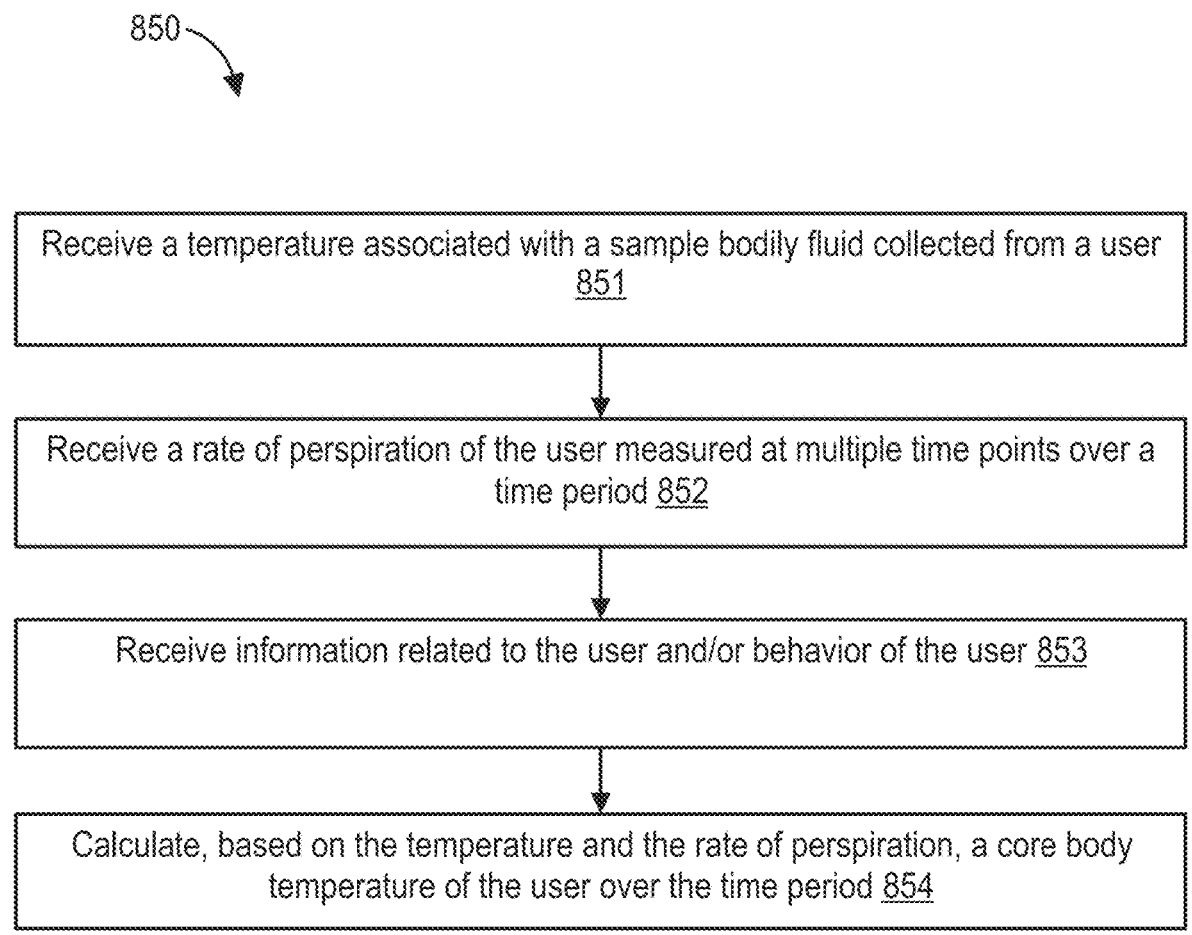
FIG. 10 is a flowchart schematically illustrating an example method of using a SA system to measure a core body temperature of a user, according to an embodiment.

In some instances, a sample handling device and/or a sample analysis system as described herein, can be used to determine a core body temperature of a user based on one or more temperature measurements made using the sample handing device. FIG. 10 is a flowchart describing an example method 850 to calculate a core body temperature of a user using a sample handling device, according to an embodiment. At 851, the method 850 includes receiving a temperature associated with a sample bodily fluid collected from a user. At 852, the method includes receiving a rate of perspiration of the user measured at multiple time points over a time period. At 853, the method 850 includes receiving information related to the user and/or information related to behavior of the user. For example, the information related to the user can include biometric, biographic, and/or physiological information. An example of information related to behavior can include information related to an activity undertaken by the user over the period of measurement (e.g., via measurements obtained from an accelerometer worn by the user), energy expended by the user over the period of measurement, and/or the like. Another example of information related to behavior can include fluid intake of the user over the period of measurement of whole-body rate of perspiration. In some implementations, however, the method 850 can use the rate of perspiration obtained at 852 as a proxy for information related to activity of the user and not require additional information related to user activity at 853.

At 854, the method 850 includes calculating, based on the temperature and the rate of perspiration, a core body temperature of the use over the time period. In some implementations, a sample analysis system can use validated sweat rate data and/or indications of levels of activity that the use is involved in to determine blood flow rate. Temperature measurement made can be skin temperature measurements of the user. In some implementations, determination of core body temperature can be based on a consideration of change in temperature from core to extremities (e.g., skin) as a function of blood flow. In some instances, the core body temperature calculated can be validated via independent methods such as using a temporal thermometer.

Figure 11:
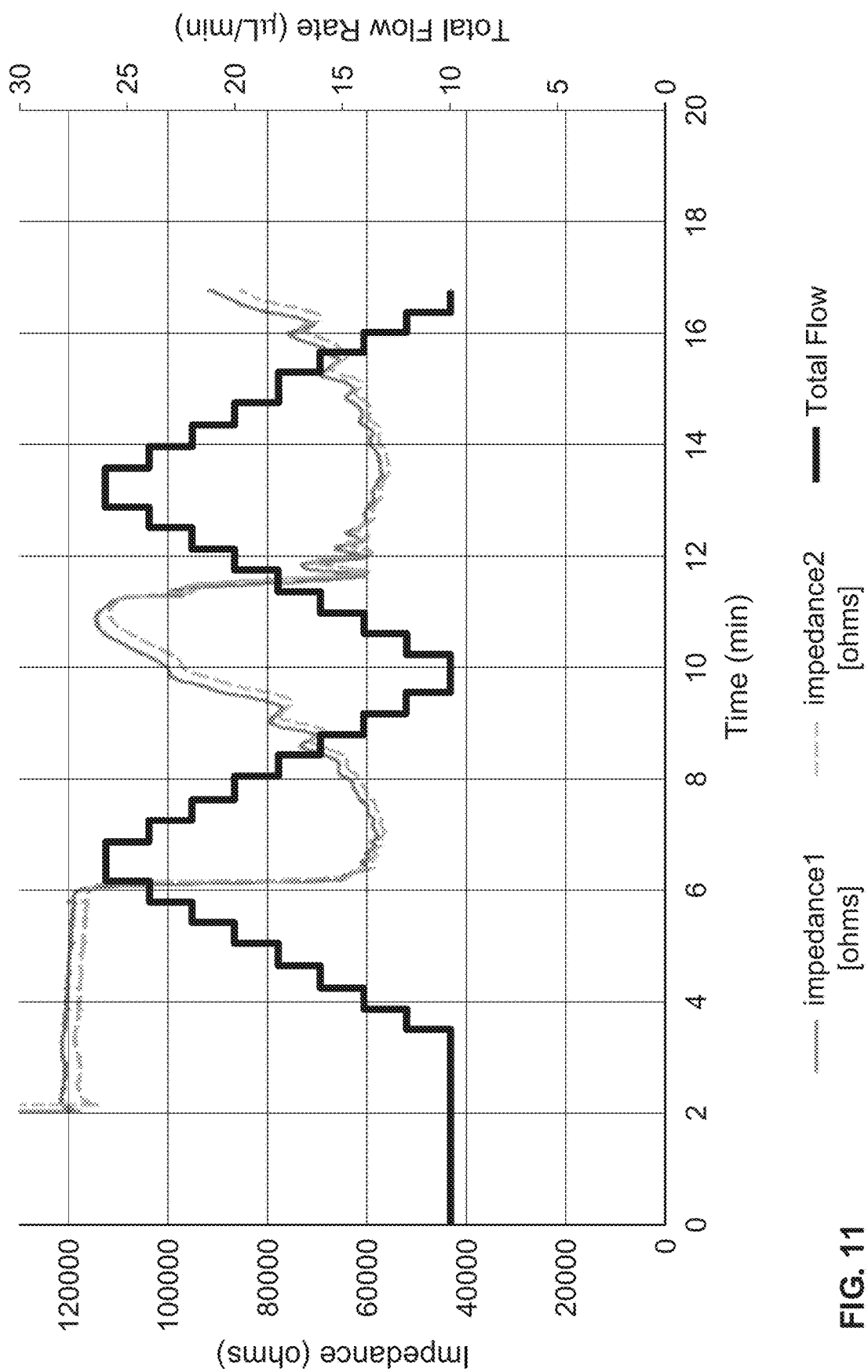
FIG. 11 is an example plot showing measurements of impedance and flow rate of a sample bodily fluid over a period of time, measured and analyzed using an example SA system, according to an embodiment.

FIG. 11 is example plot showing measurements of impedance and flow rate of a sample bodily fluid over a period of time, measured and analyzed using an example SA system, according to an embodiment. The curves indicate impedance values measured over a period of 20 minutes time and at two electrochemical interfaces (e.g., at test regions). The step plot indicates the total flow rate of the bodily fluid through the sample handling device. In some instances, a phase shift measured between the two impedance plots, as shown, is inversely proportional to the flow rate through the SA system.

Figure 12:
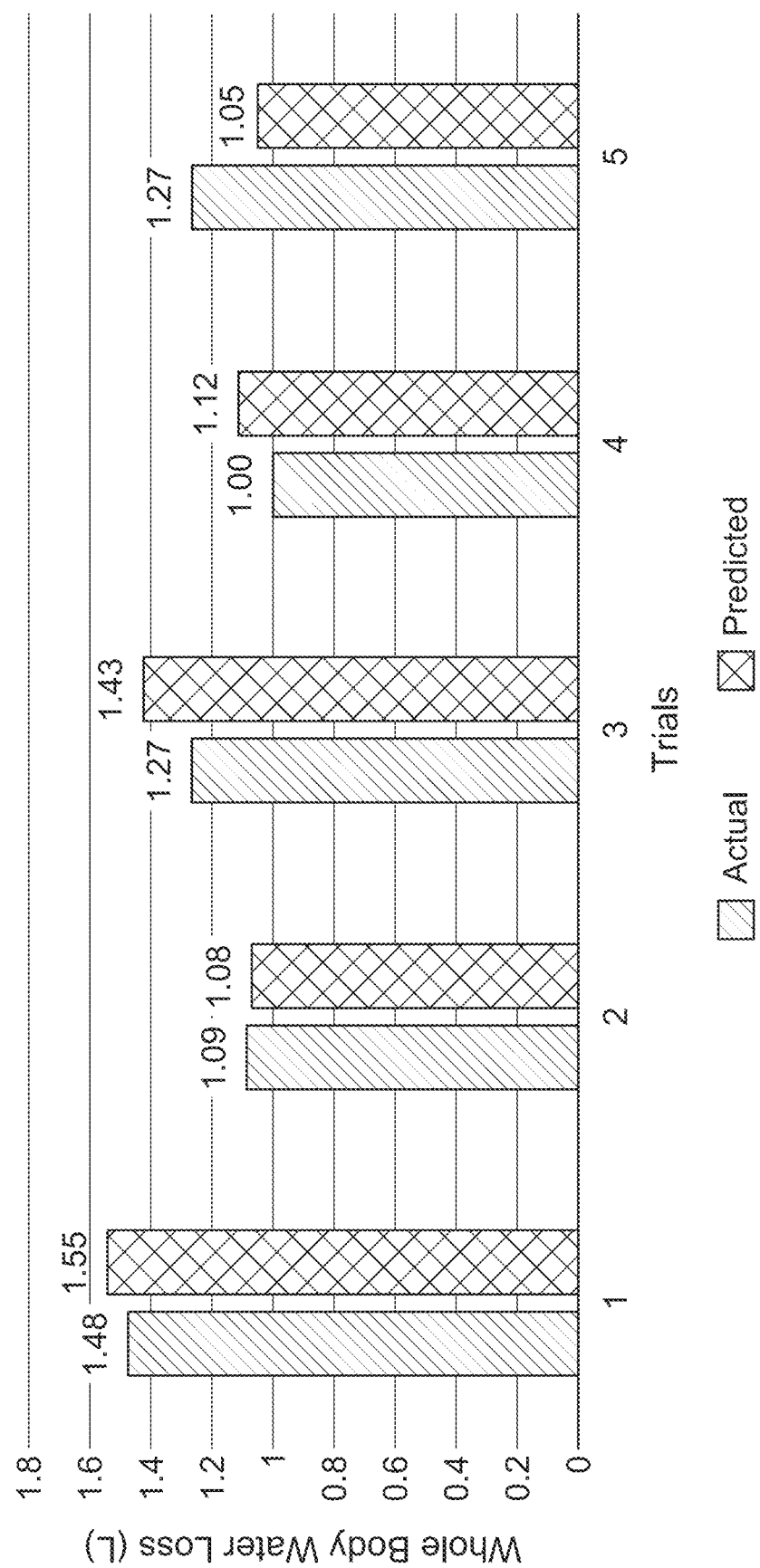
FIG. 12 is an example plot showing validation of levels of loss of body fluids predicted in subjects using an example SA system, according to an embodiment.

FIG. 12 is an example plot showing validation of levels of loss of body fluids predicted in subjects using an example SA system, according to an embodiment. Dark bars indicated actual whole body estimated of water loss and light-colored bars indicate the quality of the predictions compared to actual values.

Figure 13:
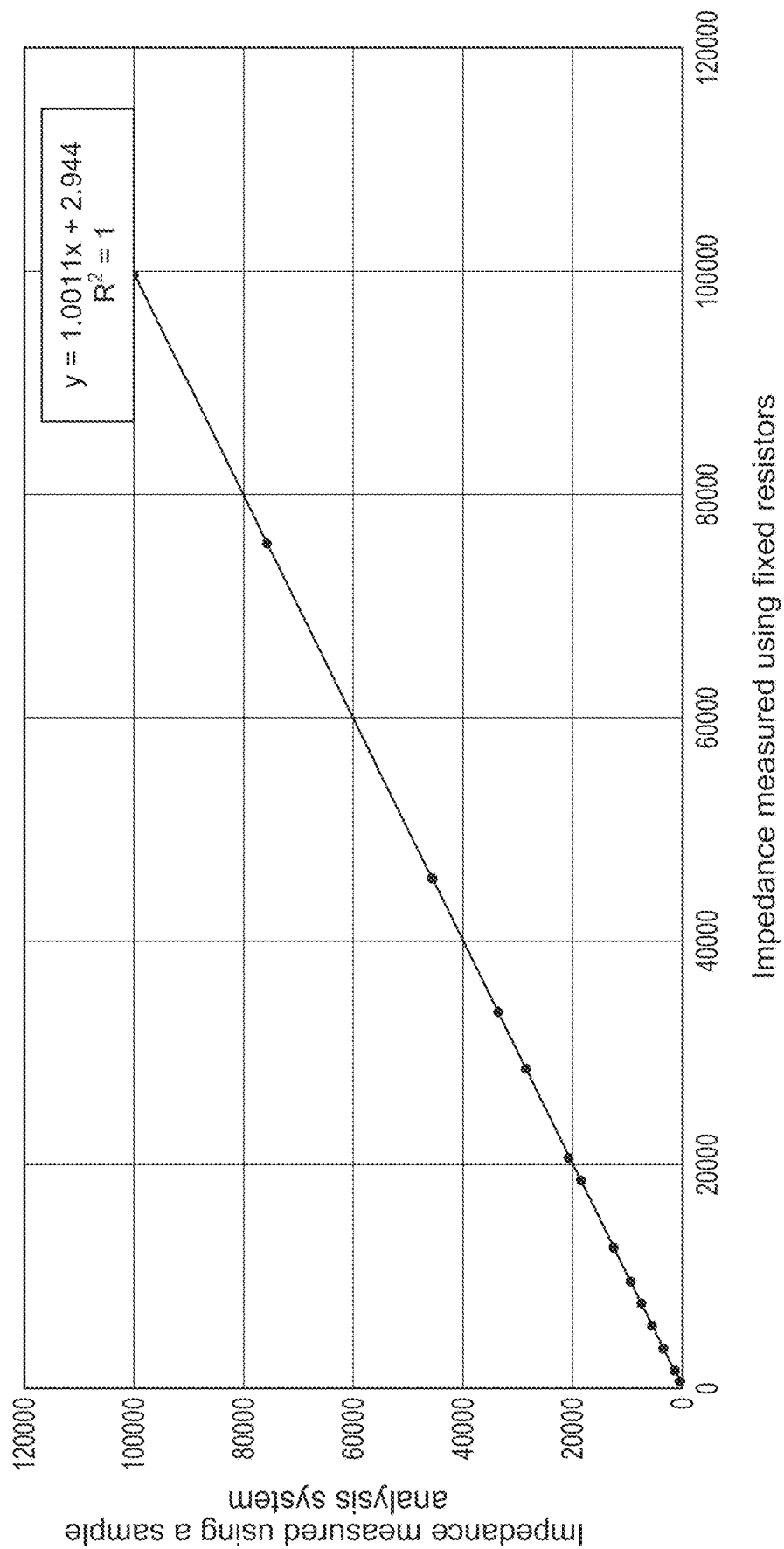
FIG. 13 is an example plot showing validation of impedance measurements associated with a bodily fluid measured using an example SA system, according to an embodiment.

FIG. 13 is an example plot showing validation of impedance measurements associated with a bodily fluid measured using an example SA system, according to an embodiment. The plot shows impedance measurements made using fixed resistors on the x-axis plotted against impedance measurements made using predictions from using a sample handling device as described herein, on the y-axis, indicating the close similarity and/or a linear relationship between the predicted and actual impedance measurements, fit with a straight line.

Figure 14:
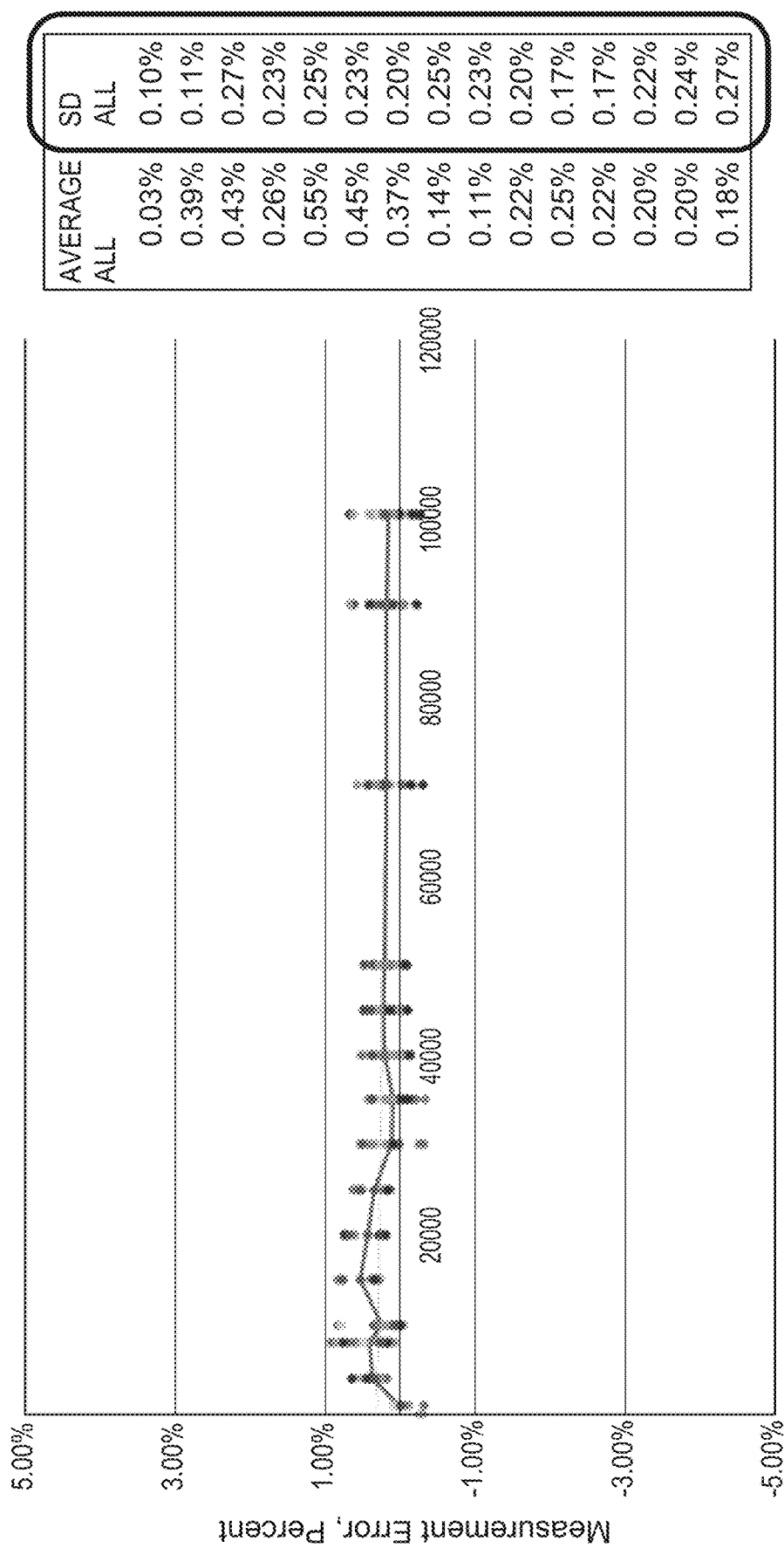
FIG. 14 is an example plot showing validation of use of an example SA system via measurement error associated with impedance measurements of a bodily fluid made using the example SA system, according to an embodiment.

FIG. 14 further indicates a plot of measurement error, estimated by comparing the predicted values and the actual measurements using independent means. FIG. 14 is an example plot showing measurement error as a function of actual impedance measurements to validate the use of an example SA system. The measurement error can be associated with impedance measurements of a bodily fluid made using the example SA system, according to an embodiment.

Figure 15:
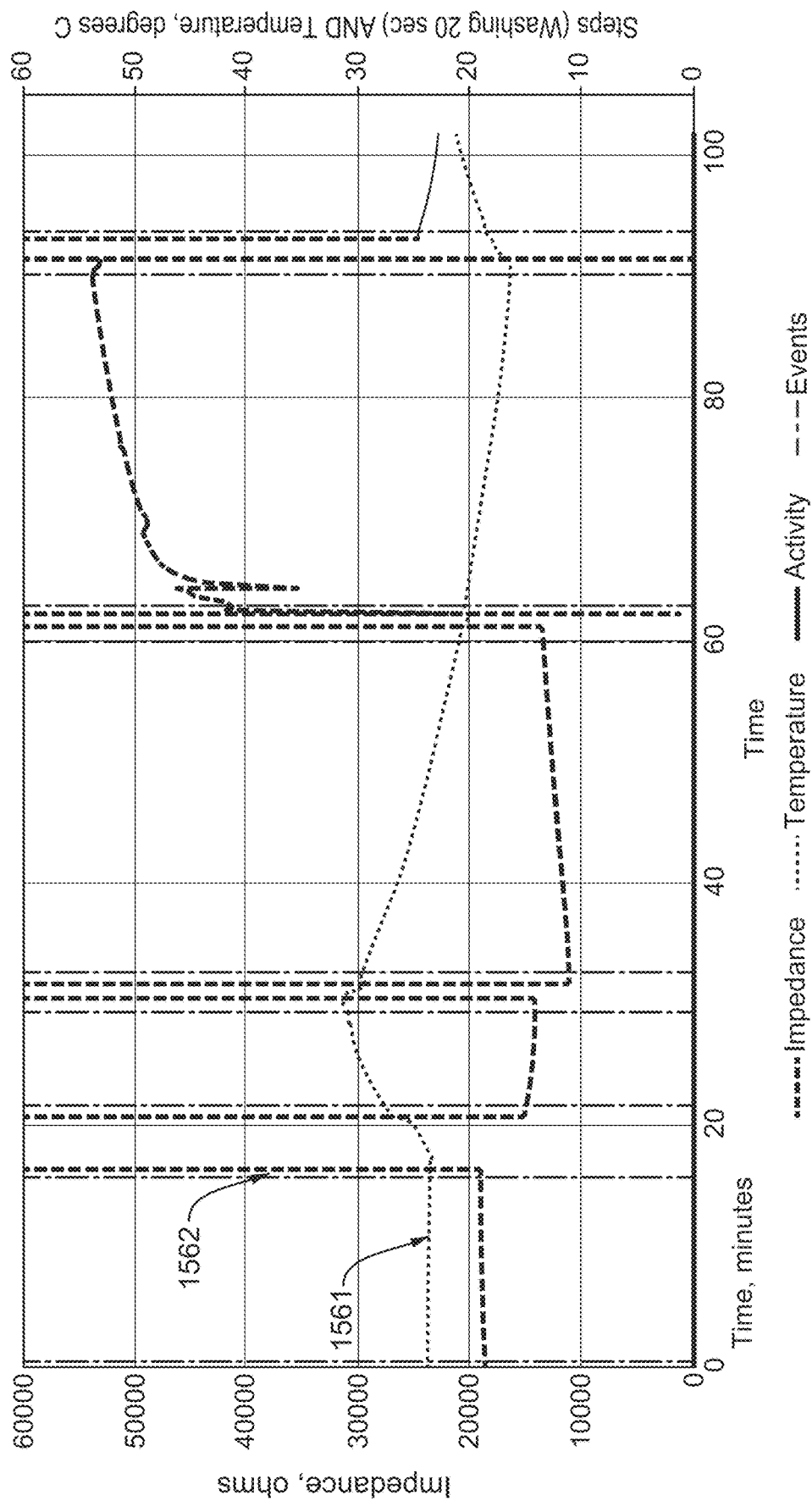
FIG. 15 is an example plot showing measurements of impedance and temperature associated with an example fluid measured using an example SA system, according to an embodiment.

FIG. 15 is an example plot showing test measurements of impedance and temperature associated with a test fluid (having a fixed osmolality) measured under controlled variation of temperature via implementing temperature sweeps, using an example SA system, according to an embodiment. The plot indicates the temperature sweeps 1561 and changes in measure impedance 1562 related to the changes in temperature as indicated by the sweep of temperature 1561.

Figure 16:
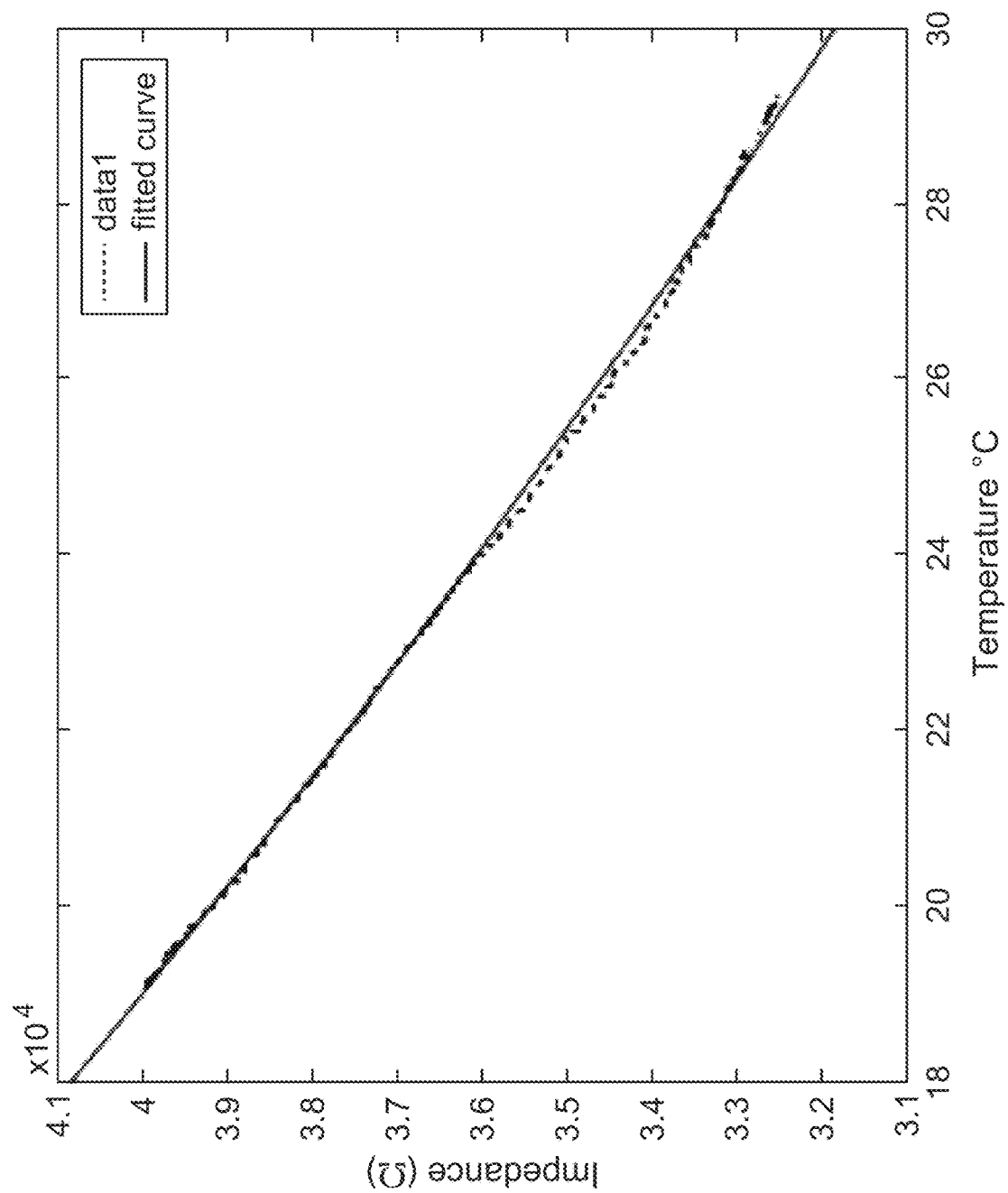
FIG. 16 an example plot showing data related to the relationship between temperature measurements and impedance measurements made using an example SA system, according to an embodiment.

FIG. 16 an example plot showing data related to the relationship between temperature measurements and measured impedance of a test fluid of known osmolality, calculated using an example SA system, according to an embodiment. For example, in some implementations, a mathematical model can be built using data collected using sample handling devices and/or other independent methods of measuring properties like impedance from sample bodily fluids. In some implementations, the mathematical model can be represented by a representation (e.g., an equation) associated with a fitted curve used to fit the model to the data. In some instances, the data can be collected during test runs with controlled conditions for example, the temperature sweeps described with reference to FIG. 15.

Figure 17:
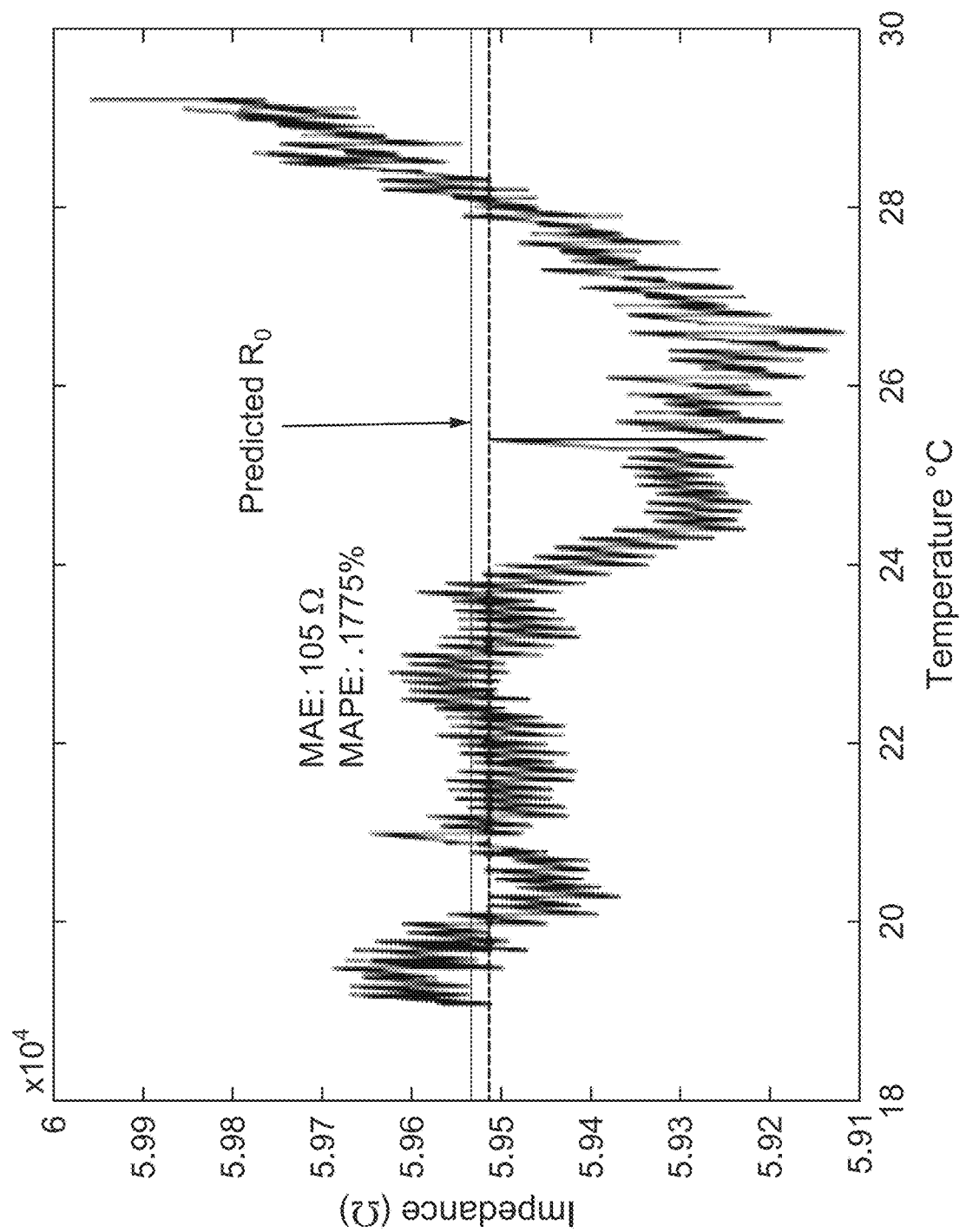
FIG. 17 an example plot showing the relationship between impedance and temperature obtained from actual measurements and predicted based on the data from a mathematical model such as the data shown in FIG. 16.

FIG. 17 an example precision analysis plot showing the relationship between impedance measured from a sample bodily fluid and temperature obtained from actual measurements. The plot also shows a predicted value of impedance indicated by the horizontal line, the prediction being based on measurements made using a sample handling device as described herein and/or data from a mathematical model such as the data shown in FIG. 16. More specifically, the plot shows that the error rate incurred while implementing temperature-correction using a SA system, according to an embodiment, is only 0.1775%.

Figure 18:
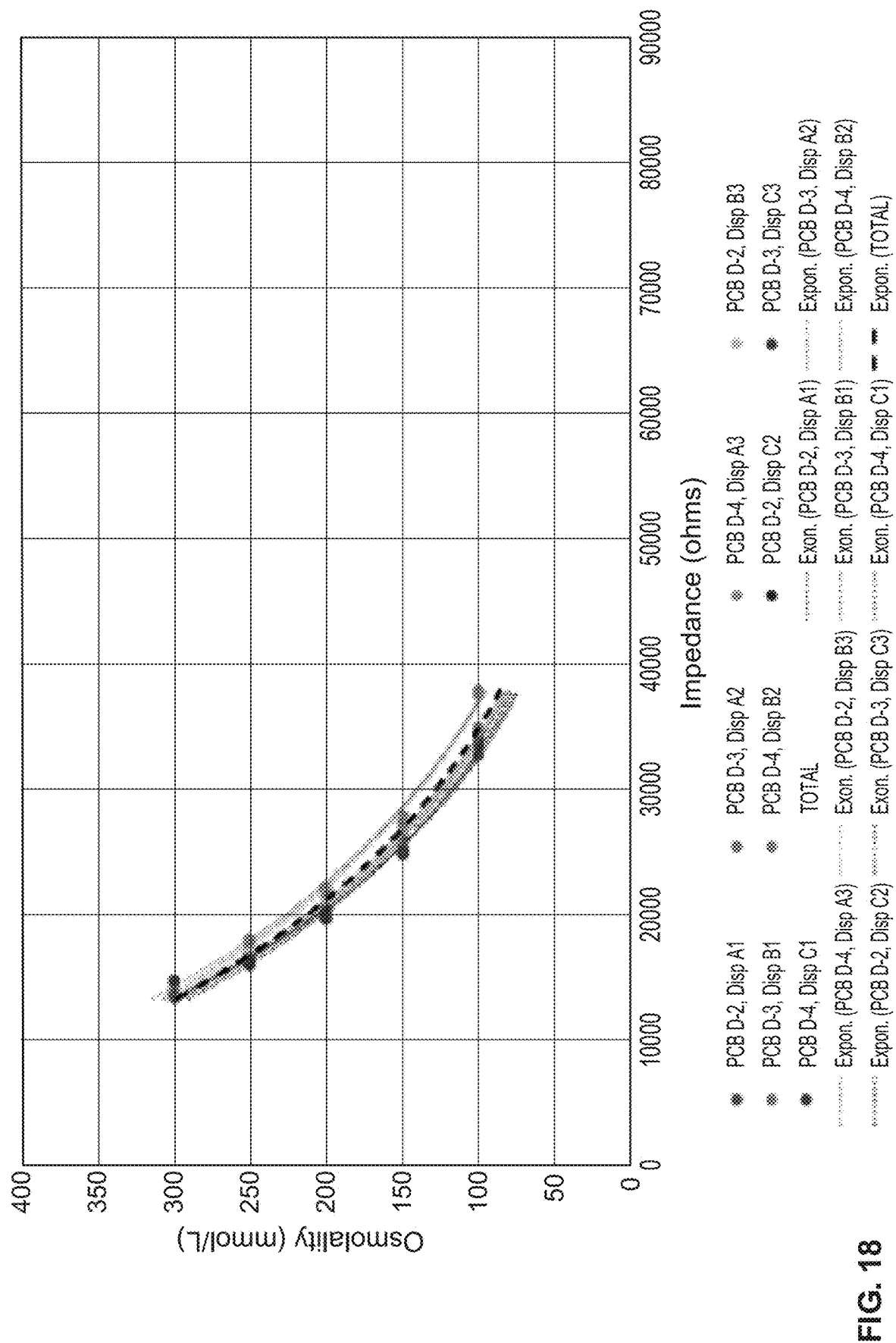
FIG. 18 an example plot showing relationship between osmolality and impedance measurements obtained from a plurality of sample fluids using example SA systems of some embodiments.

FIG. 18 an example plot used to validate conversion methods used to convert impedance measurements to osmolality. The plot in FIG. 18 shows the relationship between osmolality of a plurality of known control solutions (of known osmolality and/or electrolyte content) and impedance measurements obtained from the plurality of control solutions used as sample fluids tested by example SA systems of some embodiments. Specifically, the plot in FIG. 18 shows that an accuracy of 97.29% was obtained in calculations of osmolality based on impedance measurements obtained using a SA system, according to an embodiment, as described herein. In some instances, the plot shown can be used as a calibration curve to calibrate a SA analysis system according to some embodiments. Several such relationships can be used to develop suitable mathematical models using appropriate formula and/or equations for calibration curves that can be used to generate a model for the relationship between osmolality and impedance. In the example curves shown in FIG. 18, control solutions of known osmolality (i.e., electrolyte content) were pumped through a set of test sample analysis systems with an injection pump on a benchtop setup using several different sample processing devices, and several different sample handling devices. As described above, the best-fit curves show precision of 97.3%. The equation used to obtain the curves can serve as the algorithm to convert temp-adjusted impedance to osmolality.

Figure 19:
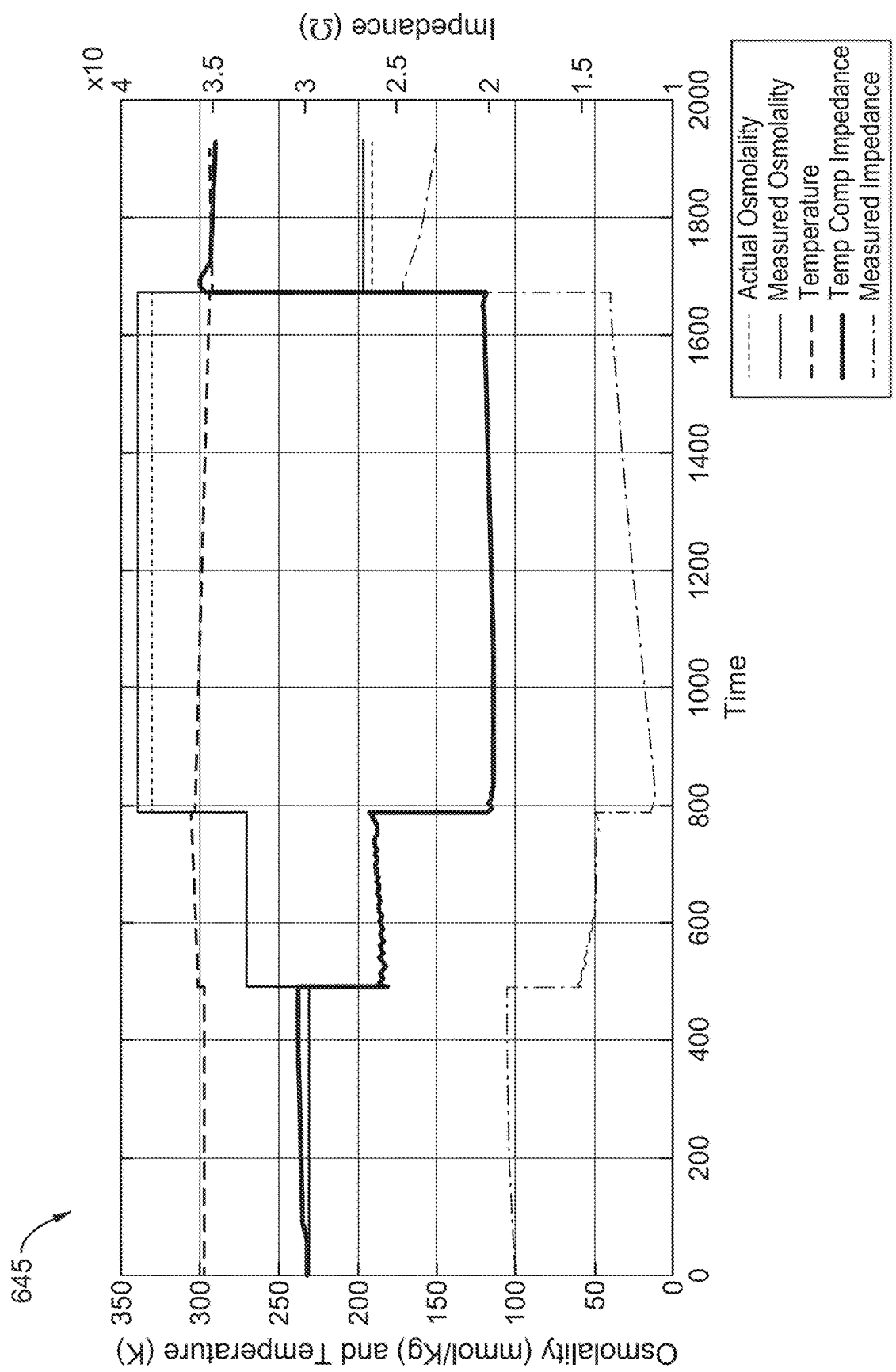
FIG. 19 an example plot showing osmolality, temperature, and impedance measurements obtained from a sample fluid over time, using a SA system, according to an embodiment.
Figure 20:
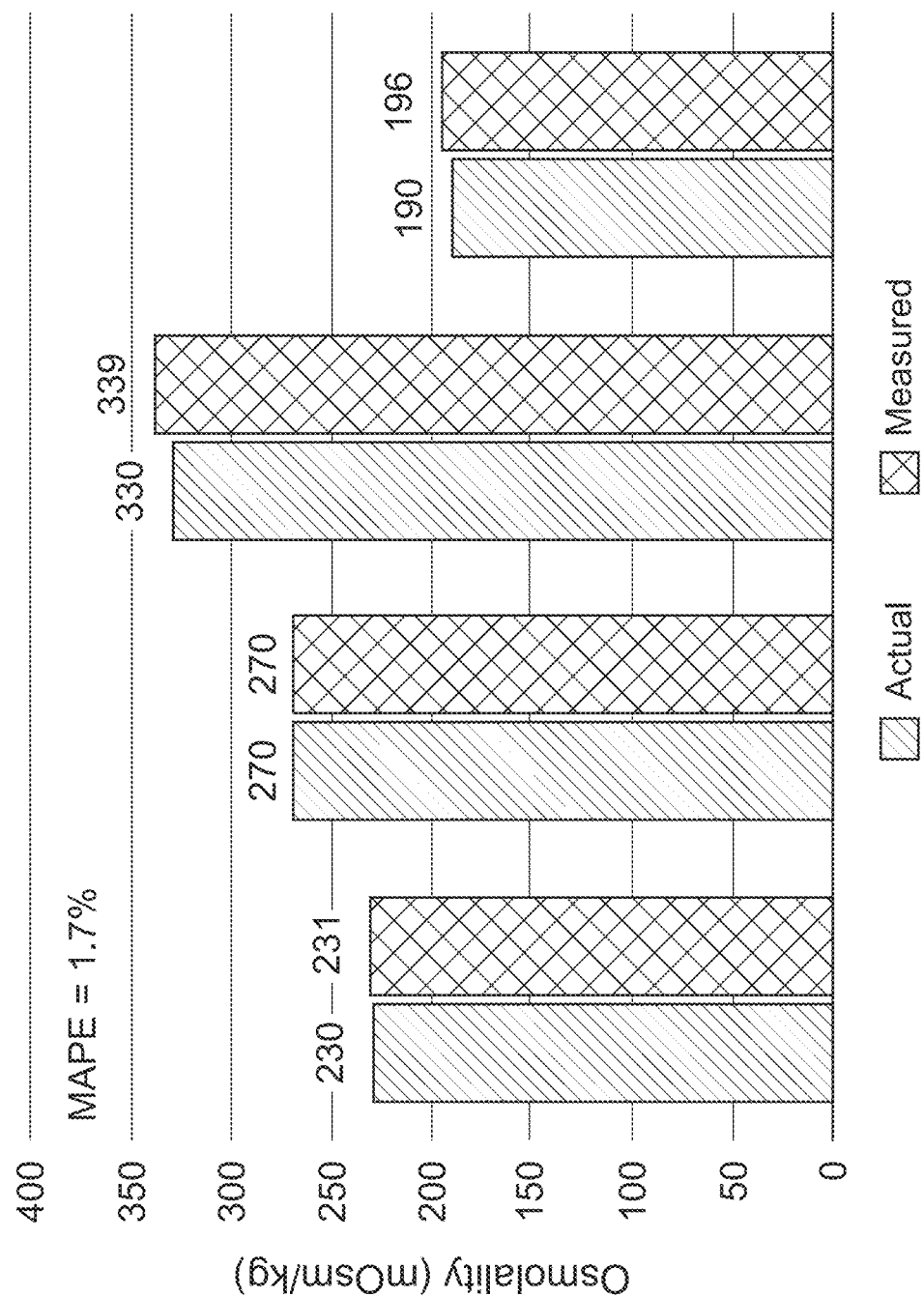
FIG. 20 an example plot showing mean absolute percent error (MAPE) values validating osmolality values predicted by a SA system, according to an embodiment, with osmolality measured using independent methods.
Figure 21:
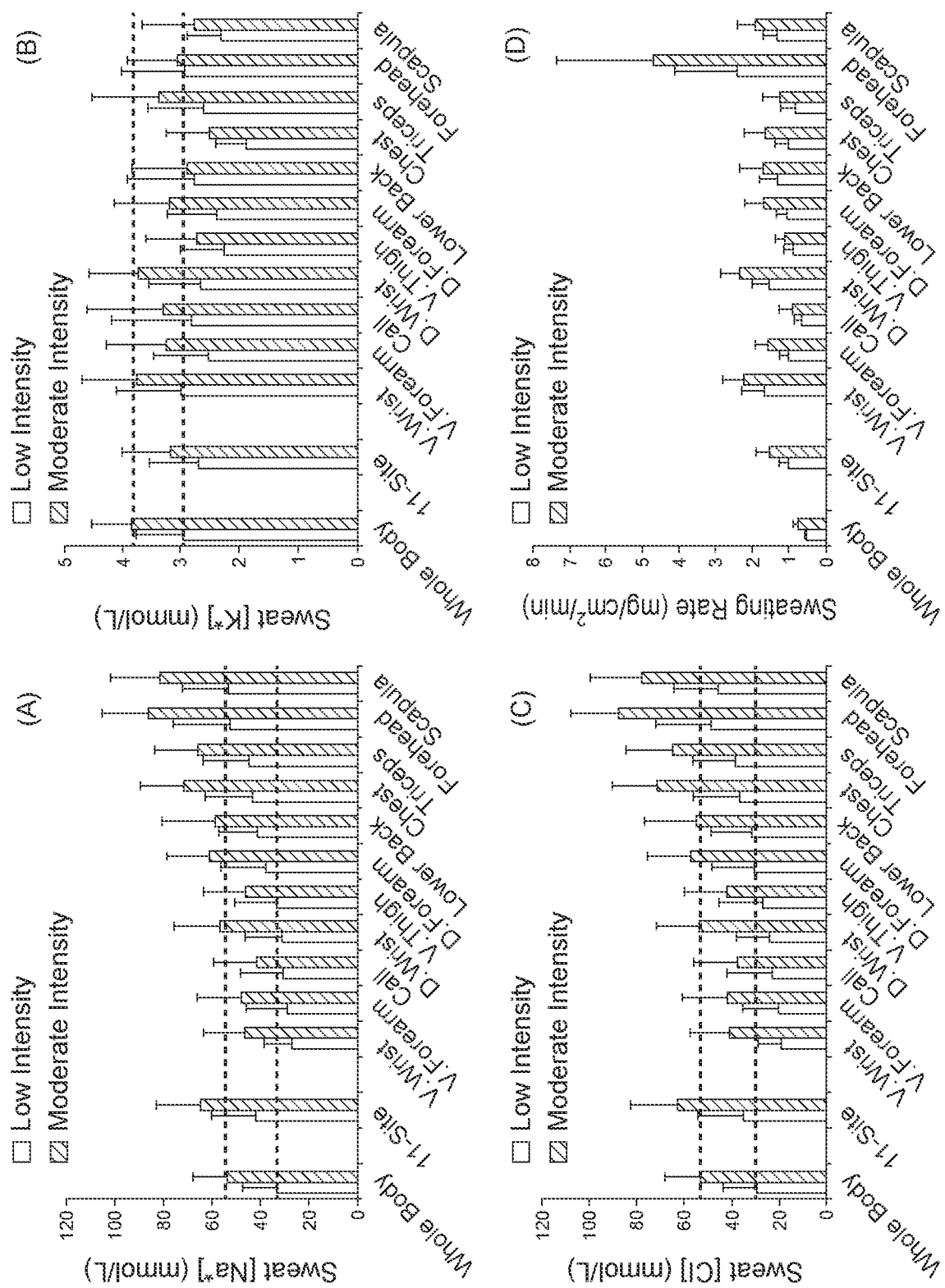
FIGS. 21A-D show example plots of ion concentration in sweat samples obtained from multiple locations of the body of users performing low and moderate levels of activity.

FIG. 19 an example plot showing osmolality, temperature, and impedance measurements obtained during a blinded osmolality test from a sample fluid over time, using a SA system, according to an embodiment. The plot shows raw impedance measurements and predicted osmolality data as measured and calculated by an example sample analysis system, compared to actual osmolality from control solutions of known osmolality. A blinded osmolality test was conducted on a benchtop setup with control solutions of known osmolality, and raw impedance values were recorded using a set of sample handling devices. Using data collected and algorithms developed the raw data were converted to temperature-corrected osmolality for a measured value. The plot in FIG. 19 shows the actual osmolality of the control solutions pumped through the test setup, and the predicted/calculated osmolality value using a SA system, according to an embodiment. FIG. 20 below shows the accuracy of the above test to be 98.3%.

FIG. 20 shows an example plot showing mean absolute percent error (MAPE) values associated with measured data (e.g., data shown in FIG. 19) validating osmolality values predicted by a SA system, according to an embodiment, with osmolality measured using independent methods. The actual and predicted values produced a mean absolute percent error (MAPE) of 1.7% (B), or precision of 98.3%, as shown in FIG. 20.

FIGS. 21A-D show example plots of ion concentrations (e.g., [Na+], [K+], [Cl−]) in sweat samples and sweating rate obtained from multiple locations of the body of users performing low and moderate levels of activity. Also shown are indications of identified levels or thresholds of ion concentrations (dashed horizontal lines) that can be used to determine optimal positioning of a sample handling device for use to obtain desired results.

FIG. 22 is an example table showing changes in ion concentration in sweat samples obtained from multiple locations of the body of users performing low and moderate levels of activity. Also shown are indications of identified locations (boxes) that can be used to determine optimal positioning of a sample handling device for use to obtain desired results FIG. 23 shows an example illustration of a companion application, as described herein, to be used with a sample handling device, according to some embodiments.

CONCLUSION

In summary, systems and methods are described herein for use in the instantaneous measurement and analysis of samples of bodily fluids to assess a property of the bodily fluid and/or a physiological/wellness parameter (e.g., degree of hydration, electrolyte losses, perspiration rate, etc.) of the user.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above. Any portion of the apparatus and/or methods described herein may be combined in any combination, except mutually exclusive combinations. The embodiments described herein can include various combinations and/or sub-combinations of the functions, components, and/or features of the different embodiments described Where methods described above indicate certain events occurring in certain order, the ordering of certain events may be modified. Additionally, certain of the events may be performed concurrently in a parallel process when possible, as well as performed sequentially as described above.

The invention claimed is:

1. A method, comprising:
    collecting a sample of bodily fluid in a sample collection region of a device;
    directing the sample of bodily fluid from the sample collection region to a first electrochemical interface, the first electrochemical interface including a first excitation electrode and a first sensing electrode;
    applying a first excitation signal from the first excitation electrode to a portion of the sample of bodily fluid present at the first electrochemical interface;
    sensing a first response signal in response to applying the first excitation signal;
    measuring, based on the first response signal and at a first time point, a first impedance data related to the portion of the sample of bodily fluid;
    directing the sample of bodily fluid from the first electrochemical interface through a flow channel to a second electrochemical interface, the second electrochemical interface including a second excitation electrode and a second sensing electrode;
    continuously and simultaneously to applying the first excitation signal, applying a second excitation signal from the second excitation electrode to the sample of bodily fluid present at the second electrochemical interface;
    sensing a second response signal in response to applying the second excitation signal;
    measuring, based on the second response signal, a second impedance data related to the sample of bodily fluid;
    comparing the second impedance data to the first impedance data to identify a second time point when the portion of the sample of bodily fluid flows past the second electrochemical interface based on a similarity between the first impedance data and the second impedance data; and
    determining, based on the similarity between the first impedance data and the second impedance data, and a difference between the second time point and the first time point, a flow rate of the portion of the sample of bodily fluid through the flow channel.

2. The method of claim 1, further comprising:
    obtaining information associated with physiology of a user;
    determining, based on the information associated with physiology of the user, and the flow rate of the portion of the sample of bodily fluid, a property of a source of bodily fluid from which the sample of bodily fluid was collected.

3. The method of claim 2, wherein the source of bodily fluid is sweat, and the property of the source of bodily fluid is perspiration rate.

4. The method of claim 3, further comprising:
    calculating, based on the perspiration rate, a cumulative fluid loss over a period of time.

5. The method of claim 4, further comprising;
    estimating, based on the cumulative fluid loss over the period of time and the information associated with physiology of a user, a full body fluid loss over the period of time.

6. The method of claim 1, further comprising:
    determining, based on the first impedance data or the second impedance data related to the portion of the sample of bodily fluid, an osmolality associated with the portion of the sample of bodily fluid;
    obtaining information associated with physiology of a user; and
    calculating, based on the osmolality and the information associated with physiology of the user, an electrolyte content associated with a source of bodily fluid from which the sample of bodily fluid was collected.

7. The method of claim 6, further comprising:
    calculating, based on the electrolyte content associated with the source of bodily fluid, a cumulative electrolyte loss over a period of time.

8. The method of claim 7, further comprising:
    estimating, based on the cumulative electrolyte loss over the period of time and the information associated with physiology of a user, a full body electrolyte loss over the period of time.

9. The method of claim 1, further comprising:
    obtaining information associated with physiology of a user;
    obtaining information associated with behavior of the user, the behavior being related to fluid intake or fluid outflow;
    determining, based on at least one of the information associated with physiology of the user, information associated with behavior of the user, or the flow rate of the portion of the sample of bodily fluid, a rate of change in hydration of the user.

10. The method of claim 1, further comprising:
    receiving a temperature associated with the sample of bodily fluid; and
    calculating, based on the temperature, a temperature-corrected first impedance data and a temperature-corrected second impedance data related to the portion of the sample of bodily fluid.

11. The method of claim 1, further comprising:
    receiving a temperature associated with a body of a user;
    obtaining information associated with physiology of the user;
    determining, based on the temperature, the information associated with physiology of the user, and the flow rate of the portion of the sample of bodily fluid, a core body temperature of the user.

12. The method of claim 1, wherein the second excitation electrode is the same as the first excitation electrode.

13. A method, comprising:
    collecting a sample bodily fluid in a sample collection region of a device;
    directing the sample bodily fluid from the sample collection region to a first electrochemical interface of the device;
    applying a first excitation signal from the first electrochemical interface;
    sensing, at a first time point, a first response signal obtained from a first portion of the sample bodily fluid, and in contact with the first electrochemical interface;
    calculating a first impedance associated with the first response signal;
    identifying a first feature associated with the first impedance;
    directing the sample of bodily fluid from the first electrochemical interface to a second electrochemical interface of the device through a flow channel;
    continuously and simultaneously to applying the first excitation signal, applying a second excitation signal from the second electrochemical interface;
    sensing a second response signal obtained from a second portion of the sample bodily fluid, in contact with the second electrochemical interface;
    calculating a second impedance associated with the second response signal;
    identifying a second feature associated with the second impedance;
    comparing the first feature with the second feature to identity a second time point when based on a similarity between the first feature and the second feature;
    receiving information related to a distance between the first electrochemical interface and the second electrochemical interface, the distance being traversed by a flow of the sample bodily fluid; and
    calculating, based on the first impedance, the second impedance, the determination of similarity, and the distance, a flow rate of the sample bodily fluid through the flow channel included in the device.

14. The method of claim 13, wherein the feature includes a phase.

15. The method of claim 13, further comprising:
    measuring a covariance between the first feature and the second feature;
    identifying a value of maximum covariance;
    comparing the value of maximum covariance with a predefined threshold value; and
    determining a measure of similarity between the first feature and the second feature.

16. The method of claim 13, wherein the sample bodily fluid includes sweat, the method further comprising:
    calculating, based on the first impedance, the second impedance, and the flow rate, a rate of perspiration of the user.

17. The method of claim 16, further comprising:
    receiving a temperature associated with the sample of bodily fluid;
    calculating, based on the temperature, a temperature-corrected first impedance and a temperature-corrected second impedance, the rate of perspiration being calculated based on the temperature-corrected first impedance and the temperature-corrected second impedance.

18. The method of claim 16, the further comprising:
    receiving a temperature associated with the user's skin;
    receiving information associated with physiology of the user;
    determining, based on the temperature, the information associated with physiology of the user, and the rate of perspiration, a core body temperature of the user.

19. The method of claim 16, further comprising:
    receiving information associated with physiology of the user;
    determining, based on the information associated with physiology of the user, and the rate of perspiration, a state of hydration of the user.

20. The method of claim 16, further comprising:
    receiving information associated with physiology of the user;
    determining, based on the information associated with physiology of the user, and the rate of perspiration, a loss of electrolytes suffered by the user.

* * * * *